(12) United States Patent
Becer et al.

(10) Patent No.: US 11,752,234 B1
(45) Date of Patent: *Sep. 12, 2023

(54) SHAPE MEMORY ADHESIVES FOR APPAREL PRODUCTS

(71) Applicant: CreateMe Technologies LLC, New York, NY (US)

(72) Inventors: Caglar Remzi Becer, Rugby (GB); Daniel John MacKinnon, Great Yeldham (GB); Yongqiang Li, Sunnyvale, CA (US)

(73) Assignee: CreateMe Technologies LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,274

(22) Filed: Jun. 30, 2022

(51) Int. Cl.
| | | |
|---|---|---|
| *A61L 15/26* | (2006.01) | |
| *D01F 6/70* | (2006.01) | |
| *B29C 61/06* | (2006.01) | |
| *C09J 133/24* | (2006.01) | |

(52) U.S. Cl.
CPC .............. *A61L 15/26* (2013.01); *B29C 61/06* (2013.01); *C09J 133/24* (2013.01); *D01F 6/70* (2013.01)

(58) Field of Classification Search
CPC ........ A61L 15/26; B29C 61/06; C09J 133/24; D01F 6/70
See application file for complete search history.

(56) References Cited

U.S. PATENT DOCUMENTS

| | | |
|---|---|---|
| 1,923,215 A | 8/1933 | Otto |
| 3,228,820 A | 1/1966 | Samson |
| 3,252,848 A | 5/1966 | Borsellino |
| 5,149,741 A | 9/1992 | Alper et al. |
| 5,156,911 A | 10/1992 | Stewart |
| 5,240,530 A | 8/1993 | Fink |
| 5,415,925 A | 5/1995 | Austin et al. |
| 5,804,011 A | 9/1998 | Dutta et al. |
| 6,471,803 B1 | 10/2002 | Pelland et al. |
| 6,547,917 B1 | 4/2003 | Misiak et al. |
| 7,220,705 B2 | 5/2007 | Hare |
| 8,592,034 B2 | 11/2013 | Rule |
| 8,658,211 B2 | 2/2014 | Rozema et al. |
| 8,782,812 B2 * | 7/2014 | Bansal ................ B29C 65/4845 428/57 |
| 10,017,899 B2 | 7/2018 | Reutelingsperger et al. |
| 10,099,458 B2 | 10/2018 | Haq et al. |
| 10,377,922 B2 | 8/2019 | Kim |
| 10,458,047 B2 | 10/2019 | Keh |
| 10,646,614 B2 | 5/2020 | Grinstaff et al. |
| 10,731,053 B2 | 8/2020 | Himmelberger et al. |
| 2001/0031367 A1 | 10/2001 | Gilbert |
| 2004/0005832 A1 | 1/2004 | Neculescu et al. |
| 2004/0116014 A1 | 6/2004 | Soerens et al. |
| 2007/0015902 A1 | 1/2007 | Rappoport et al. |
| 2007/0281126 A1 | 12/2007 | Lahann et al. |
| 2010/0160497 A1 | 6/2010 | Karjala et al. |
| 2016/0120247 A1 | 5/2016 | Topolkaraev et al. |
| 2016/0284449 A1 | 9/2016 | Haq et al. |
| 2017/0129999 A1 | 5/2017 | Messersmith et al. |
| 2018/0094115 A1 | 4/2018 | Martz et al. |
| 2018/0362766 A1 | 12/2018 | Gee et al. |
| 2019/0092880 A1 | 3/2019 | Harada et al. |
| 2020/0056038 A1 | 2/2020 | Grinstaff et al. |
| 2020/0407608 A1 | 12/2020 | Brown et al. |
| 2021/0129487 A1 | 5/2021 | Huang et al. |
| 2021/0292482 A1 | 9/2021 | Bowman et al. |
| 2021/0380848 A1 | 12/2021 | Zhao et al. |
| 2022/0315805 A1 | 10/2022 | Kim |

FOREIGN PATENT DOCUMENTS

| | | |
|---|---|---|
| CA | 2299353 A1 | 2/1999 |
| CN | 104610587 B | 8/2016 |
| EP | 3737711 A1 | 11/2020 |
| JP | 2011500975 A | 1/2011 |
| KR | 102090058 B1 | 3/2020 |
| KR | 2021-0036164 A | 4/2021 |
| KR | 20210036164 A | 4/2021 |
| KR | 102250432 B1 | 5/2021 |
| WO | 2010144774 A2 | 12/2010 |
| WO | 2012078826 A2 | 6/2012 |
| WO | 2013162019 A1 | 10/2013 |
| WO | 2017206671 A1 | 12/2017 |
| WO | 2020159823 A1 | 8/2020 |

OTHER PUBLICATIONS

Wu et al. "Four-dimensional printing of a novel acrylate-based shape memory polymer using digital light processing" in Materials and Designs 2019. (Year: 2019).*

Zhanbin Feng et al., "Photothermal-Induced Self-Healable and Reconfigurable Shape Memory Bio-Based Elastomer with Recyclable Ability," ACS App. Mater. Interfaces, Dated: Dec. 28, 2018, pp. 1469-1479.

Zhanbin Feng et al., "Multifunctional Vitrimer-Like Polydimethylsiloxane (PDMS): Recyclable, Self-Healable, and Water-Driven Malleable Covalent Networks Based on Dynamic Imine Bond," Ind. Eng. Chem. Res, Dated Jan. 10, 2019, pp. 1212-1221.

Zhou et al., "Light-Switchable Polymer Adhesive Based on Photoinduced Reversible Solid-to-Liquid Transitions", ACS Macro Lett. 2019, 8, pp. 968-972.

Yamaguchi et al., "Photoswitchable gel assembly based on molecular recognition", Nature Communications, Published Jan. 3, 2012, 5 pages.

(Continued)

*Primary Examiner* — Blessing M Fubara

(57) ABSTRACT

Embodiments provide an apparel product. The apparel product includes a major component forming a base portion of the apparel product and is configured to be supported and worn at least partially over a portion of a wearer. The apparel product includes a minor component forming a secondary portion configured to be coupled to the major component. An adhesive is disposed at least partially between a portion of the major component and a portion of the minor component. The adhesive includes a shape memory material.

20 Claims, 4 Drawing Sheets

(56) References Cited

OTHER PUBLICATIONS

Daniel Hendrik Turkenburg et al., "Polyurethane adhesives containing Diels-Alder-based thermoreversible bonds," Journal of Applied Polymer Science, dated Feb. 16, 2017 [Abstract Only].
"Adhesive Bonding: Thermally Removable Adhesive Bonds," Assembly, Dated Feb. 1, 2003 https://www.assemblymag.com/articles/86029-adhesive-bonding-thermally-removable-adhesive-bonds#:~:text=The%20bond%20is%20broken%20by,The%20disassembled%20foams%20are%20intact.
R. Araya-Hermosilla et al., "Reversible Polymer Networks Containing Covalent and Hydrogen Bonding Interactions," Science Direct, European Polymer Journal, vol. 50, Dated Jan. 2014, pp. 127-134 [Abstract Only].
Jingjing Chen et al., "Reversibly Cross-Linked Fullerence/Polyamide Composites based on Diels-Alder Reaction," ScienceDirect, Composites Science and Technology, vol. 176, Dated May 26, 2019, pp. 9-16 [Abstract Only].
Sridhar et al. (2020) Re-usable thermally reversible crosslinked adhesives from robust polyester and poly(ester urethane) Diels—Alder networks. Green Chemistry, 22 (24). pp. 8669-8679. ISSN 1463-9262.
Hyesung Cho et al., "Intrinsically Reversible Superglues via Shape Adaptation Inspired by Snail Epiphragm," PNAS, vol. 116, No. 28, Dated Jul. 9, 2019, pp. 13774-13779.
Joe Charbonnet et al., "New Approaches in Cotton Crosslinking," Greener Solutions, Year: 2013, pp. 1-71.
Amir Mahmoud Asadirad et al., "Controlling a Polymer Adhesive Using Light and a Molecular Switch," ACS Publications, Dated Feb. 12, 2014, pp. 3024-3027 [Abstract Only].
Junyu Ren et al., "Dynamic reversible adhesives based on crosslinking network via Schiff base and Michael addition," RCS Advances, Dated May 18, 2022, pp. 1-10.
Benjamin Gyarmali et al., "Reversible Disulphide Formation in Polymer Networks: A Versatile Functional Group from Synthesis to Applications," European Polymer Journal 49 (2013) 1268-1286.
Paul J. Bracher et al., "The Relative Rates of Thiol-Thioester Exchange and Hydrolysis for Alkyl and Aryl Thioalkanoates in Water," Orig Life Evol Biosph, Prebiotic Chemistry, Dated: Jul. 5, 2011, pp. 399-412.
Marlena D. Konieczynska et al., "On-Demand Dissolution of a Dendritic Hydrogel-based Dressing for Second-Degree Burn Wounds through Thiol-Thioester Exchange Reaction," Agnew Chem. Int. Ed. Year: 2016, pp. 9984-9987.
Julie Thevenot et al., "Magnetic Responsive Polymer Composite Materials," Chem. Soc. Rev. Dated: May 2, 2013, pp. 7099-7116.
Chen Wang et al., "Recyclable and Repolymerizable Thiol-X Photopolymers," Materials Horizons, Year: 2018, pp. 1042-1046.
Brady T. Worrell et al., "Bistable and Photoswitchable States if Matter," Nature Communications, Year: 2018, pp. 1-7.
Felipe Orozco et al., "Diels-Alder-based thermo-reversibly crosslinked polymers: Interplay of Crosslinking Density, Network Mobility, Kinetics and Stereoisomerism," ScienceDirect, European Polymer Journal, Year: 2020, Pates: 1-8.
Max Rottger et al., "High-Performance Vitrimers From Commodity Thermoplastics Through Dioxaborolane Metathesis," Science, Dated: Apr. 7, 2017, pp. 62-65.
Brady T. Worrell et al., "A User's Guide to the Thiol-Thioester Exchange in Organic Media: Scope, Limitations, and Applications in Material Science," Polymer Chemistry, Dated: Aug. 6, 2018, pp. 1-15.
Natalie Artzi et al., "Aldehyde-Amine Chemistry Enables Modulated Biosealants with Tissue-Specific Adhesion," Advanced Materials, Year: 2009, pp. 1-5.
Takahiro Kakuta et al., "Adhesion between Semihard Polymer Materials Containing Cyclodextrin and Adamantane Based on Host-Guest Interactions," Macromolecules, ACS Publications, Dated: Jan. 29, 2015, pp. 732-738.
Arzt, M., Seidler, C., Ng, D. Y. W., & Weil, T. (2014). Reversible Click Reactions with Boronic Acids to Build Supramolecular Architectures in Water. Chemistry—An Asian Journal, 9(8), 1994-2003. doi:10.1002/asia.201402061.
Bull et al., "Exploiting the Reversible Covalent Bonding of Boronic Acids: Recognition, Sensing, and Assembly," Accounts of Chemical Research, Dated May 15, 2012, pp. 312-326.
Narkar, A. R., & Lee, B. P. (2018). Incorporation of anionic monomer to tune the reversible catechol-boronate complex for pH responsive, reversible adhesion. Langmuir. http://dx.doi.org/10.1021/acs.langmuir.8b00373.
Sijia Huang et al., "Chemically Recycling Poly(thiourethane) Thermosets Enabled by Dynamic Thiourethane Bonds," Polymer Chemistry dated Sep. 11, 2020, pp. 1-6.

* cited by examiner

SHAPE MEMORY ADHESIVES FOR APPAREL PRODUCTS

FIELD

The present disclosure is directed to apparel products, methods of assembling apparel products, and methods of disassembling apparel products.

BACKGROUND

Apparel products are made from various components and each component can include different polymer materials. After use, the apparel products are often found in landfills contributing to waste even though many of the apparel products include materials that still retain structural integrity. There has been an increasing effort to recycle, reuse, and reduce products across many industries. However, recycling apparel products can be a challenge due to the mix of materials used in the various components which must be separated to enable recycling. In the apparel industry, the components of apparel products are often joined together by sewing or other permanent methods and are difficult to disassemble manually or automatically which typically makes recycling of the components prohibitively time consuming or costly. Separating the components is possible by manual separation to ensure separating the components while maintaining the integrity of the materials to be collected and recycled. Manual separation cannot keep up with the high volume of apparel products that are to be recycled and reused and is often costly. Moreover, forming apparel products that enable streamlined separation also needs to be streamlined at large scale.

Therefore, there is a need for apparel products that are easily assembled and are easy to disassemble and methods of manufacturing and/or disassembling the apparel products.

SUMMARY

In some embodiments, an apparel product is provided. The apparel product includes a major component forming a base portion of the apparel product and is configured to be supported and worn at least partially over a portion of a wearer. The apparel product includes a minor component forming a secondary portion configured to be coupled to the major component. An adhesive is disposed at least partially between a portion of the major component and a portion of the minor component. The adhesive includes a shape memory material.

In some embodiments, an apparel product is provided. The apparel product includes a major component of the apparel product. The major component forms a base portion of the apparel product and is configured to be supported and worn at least partially over a portion of a wearer. The apparel product includes a minor component forming a secondary portion configured to be coupled to the major component. The apparel product includes an adhesive disposed on a portion of the major component or the minor component of the apparel product. The adhesive includes a polymer, a shape memory material, and a plurality of particles.

In some embodiments, an apparel product is provided. The apparel product includes a major component forming a base portion of the apparel product and is configured to be supported and worn at least partially over a portion of a wearer. The apparel product includes a minor component forming a secondary portion configured to be coupled to the major component. An adhesive is disposed on a portion of the major component or the minor component of the apparel product. The adhesive includes a polymer doped with shape memory material having a first state.

BRIEF DESCRIPTION OF THE DRAWINGS

So that the manner in which the above recited aspects are attained and can be understood in detail, a more particular description of embodiments described herein, briefly summarized above, may be had by reference to the appended drawings.

It is to be noted, however, that the appended drawings illustrate typical embodiments and are therefore not to be considered limiting; other equally effective embodiments are contemplated.

DETAILED DESCRIPTION

The present disclosure is directed to apparel products, methods of assembling apparel products, and methods of disassembling apparel products. As used herein, an "apparel product," refers to an article that is configured to fit over a portion of a body or is an accessory of an article configured to fit over the portion of the body. An apparel product includes, without limitation, clothing (e.g., shirts, pants, jeans, slacks, skirts, coats, dresses, sweaters, activewear, athletic, aerobic, exercise apparel, swimwear, cycling jerseys or shorts, race suits, wetsuits, and body suits), footwear (e.g., socks, shoes, boots, loafers), protective apparel (e.g., lab coat, flame retardant clothing), clothing accessories (e.g., hats, masks, scarves, belts, bra straps, side panels, gloves, hosiery, leggings, orthopedic braces, labels, buttons, pockets, purses, tags, security tag, neck ties, bowties) undergarments (e.g., underwear, t-shirts, tank tops, shapewear), compression garments, draped garments (e.g., kits, loincloths, togas, ponchos, cloaks shawls), among others. An apparel product can also include accessories that can be supported or carried by a wearer, such as handbags, backpacks, totes, umbrellas, among others.

Figure 1A:
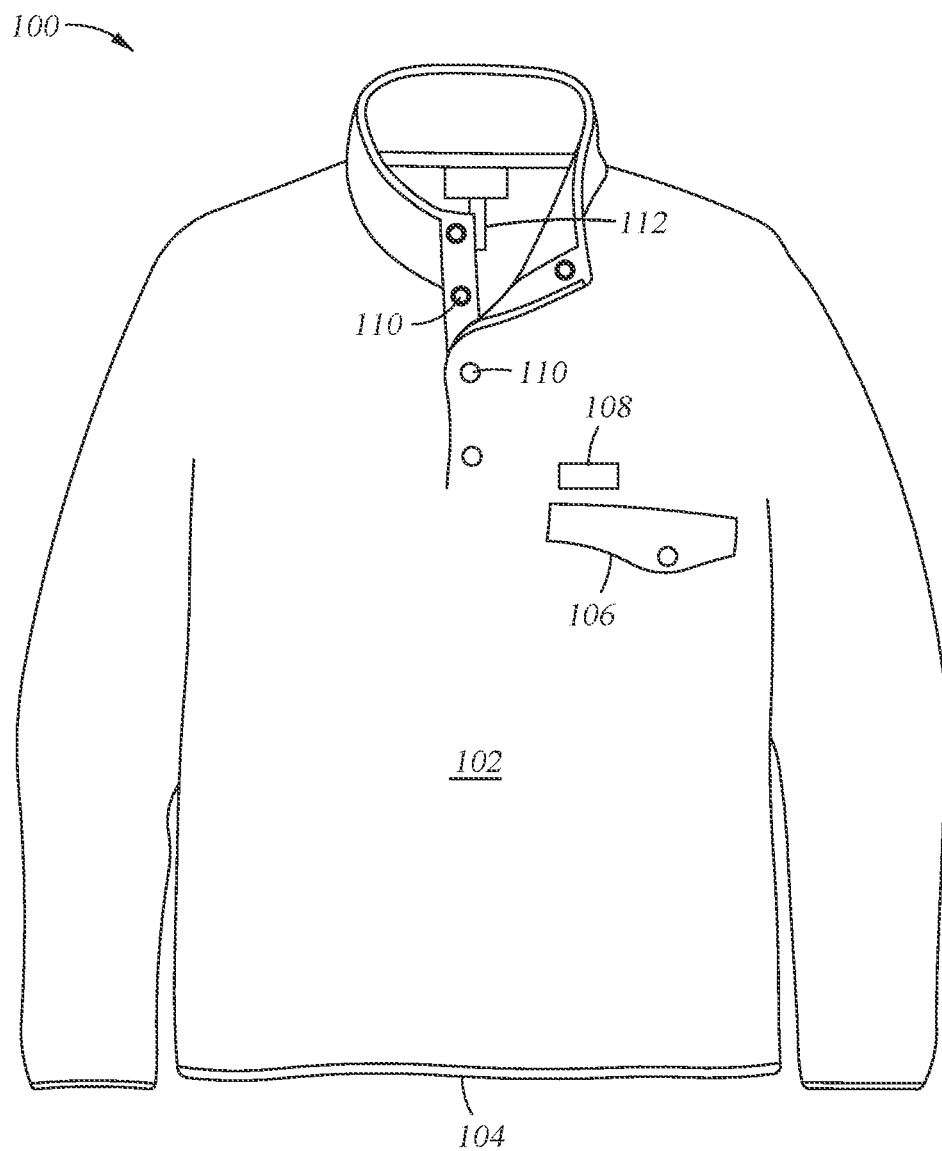
FIG. 1A depicts an apparel product according to some embodiments of the present disclosure.

FIG. 1A depicts an apparel product 100, according to some embodiments. Although the apparel product 100 depicts a long sleeved pull over shirt, any other types, shapes, and uses of articles are also contemplated. As used herein, an apparel product refers to an article that is formed from a laminate and/or layered material including layers of fabric material, a polymer sheet, or combination thereof. The apparel product can be formed from knitted, woven, or non-woven textile materials. An apparel product can be shaped to conform over at least a portion of a human body.

The apparel product 100 includes a major component 102 and additional minor components coupled to the major component 102 and/or coupled to other minor components. As used herein, "components" refer to portions of an apparel product that can be combined or joined to one another to form the apparel product. A "major component" forms a base portion of the apparel product to which one or more minor components are bonded therewith. A "minor component" includes portions of the apparel product that can be coupled to one another and/or to the major component to form the apparel product. As used herein, a minor component includes less material (e.g., fabric) than a major component. Similarly, major component includes more material (e.g., fabric) than a minor component.

In some embodiments, the major component 102 can include cotton or a polymer material, such as polyethylene terephthalate (PET) or a polyamide, such as nylon 6,6. In some embodiments, the major component 102 can be fleece, such as fleece made up of polyester fibers, polyamide fibers, or combination thereof. As used herein, the term "fleece" refers to one or more layers of strand or threads of textile materials, such as chemical fibers, natural fibers, or combinations thereof. In some embodiments the fleece can be composed of polyester, polyamide, cellulose regeneration and/or lignin fibers, such as natural fibers, wool, cotton, or combinations thereof. The fibers can be short fibers or long continuous fibers. Each of the minor components can be composed of the same or different materials from the major component. In some embodiments, one or more of the minor components can be composed of a contrasting material such as nylon. In some embodiments, the minor components can include a pocket 106 composed of the same or different material from the major component 102. The pocket 106 can be composed of a contrasting material such as nylon. The minor components can include labels 108 which can be composed of polyethylene terephthalate (PET). The labels 108 can include trademarks, logos, branding or designs. The minor components can include bindings 104 formed along edges of the major component 102, such as at the cuffs. In some embodiments, the bindings 104 are composed of nylon, spandex, or a combination thereof.

The minor components can further include fasteners 110, such as buttons or snaps. The fasteners 110 can include a recyclable thermoplastic, such as polymers such as polyacetal (e.g., commonly referred to as acetal or polyoxymethylene or POM). In some embodiments, the fasteners 110 include about 5 wt. % to about 80 wt. % PET by weight, such as about 10 wt. % to about 70 wt. %, such as about 20 wt. % to about 60 wt. %, such as about 30 wt. % to about 50 wt. %. The minor components can be coupled to the major component 102 on an outside surface of the major component 102 or on an inside surface of the major component 102. The minor components can include hanger loops 112 which can be composed of nylon. The hanger loops 112 are configured to receive a hanger or a hook. Other components are also contemplated, such as liners, shells, and design features. In some embodiments, the major component 102 includes one or more recyclable materials and one or more of the minor components include one or more recyclable materials that are different or the same as one or more of the recyclable materials of the major component 102. In some embodiments, the major component 102 includes one or more recyclable materials and one or more of the minor components include non-recyclable materials. In some embodiments, the major component 102 includes one or more non-recyclable materials and one or more of the minor components include one or more recyclable materials.

Figure 1B:
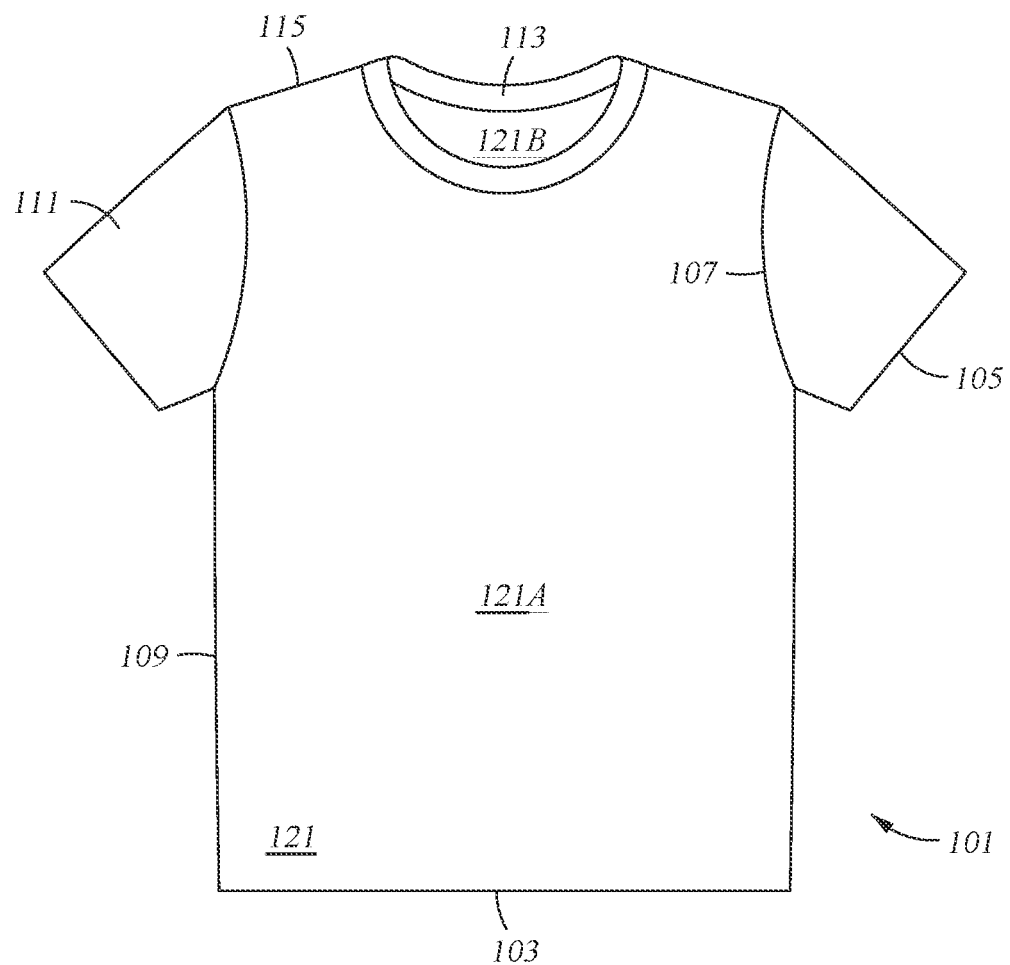
FIG. 1B depicts another apparel product according to some embodiments of the present disclosure.

FIG. 1B depicts another apparel product 101, according to some embodiments. The apparel product 101 can include a major component 121, or a plurality of major components that are shaped to conform over at least a portion of a wearer, such as human body. The major component 121 can be a continuous base portion that is configured to conform over at least a portion of a wearer. Alternatively, the major component 121 includes a plurality of portions, such as a front body panel 121A and a back body panel 121B of the major component 121. The front body panel 121A can be coupled to the back body panel 121B at seams 109, 115 using the reversible adhesives described herein, alternatively or additionally, one or more other methods, such as sewing. The major component 121 is configured to be coupled with minor components, such as a collar 113 or a sleeve 111 via interface 107. In some embodiments, one or more of the minor components are formed at least partially over at least a portion of the wearer. In some embodiments, the collar 113 is formed from coupling a first portion of a major component to a second portion of the major component by folding over the major component along a fold parallel to an edge of the major component. The major component is folded to contact the first portion to the second portion via the reversible adhesive described herein. Alternatively or additionally, one or more other methods are used to couple the first portion to the second portion of the major component, such as by sewing. In some embodiments, a folded edge 103 is formed from coupling a third portion of a major component to a fourth portion of the major component by folding over the major component along the fold edge 103 parallel to an edge of the major component. The major component is folded to contact the third portion to the fourth portion via the reversible adhesive described herein. Alternatively or additionally, one or more other methods are used to couple the third portion to the fourth portion of the major component, such as sewing.

Figure 2:
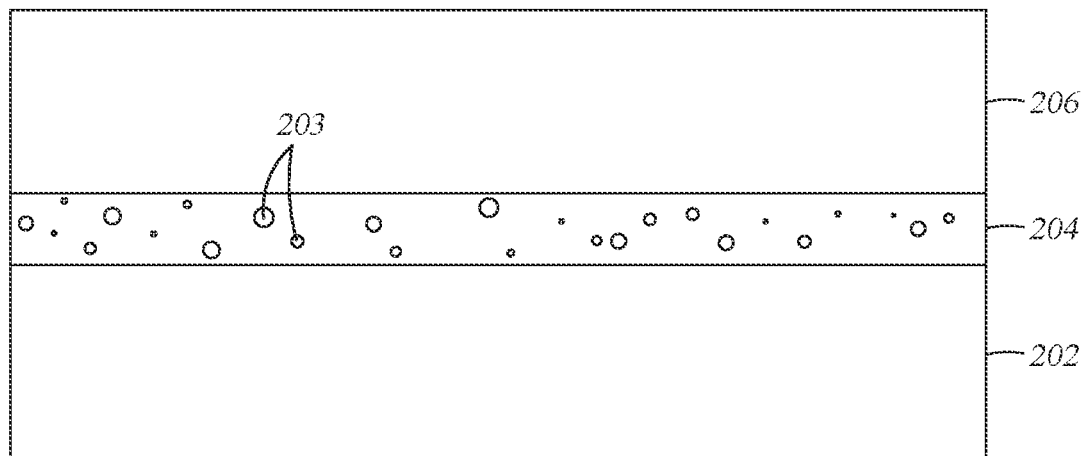
FIG. 2 depicts a portion of a major component coupled to a portion of a minor component according to some embodiments of the present disclosure.

FIG. 2 depicts a portion of a major component 202 coupled to a portion of a minor component 206. The major component 202 and the minor component 206 can be coupled by a reversible adhesive 204. In some embodiments, the reversible adhesive 204 is disposed at least partially between the minor component 206 and the major component 202. In some embodiments, the reversible adhesive is at least partially disposed or embedded within pores of the major component 202 and/or pores of the minor component 206.

The reversible adhesive 204 is capable of maintaining adhesion to the major component 202 and minor component 206 under conditions in which the apparel article is worn, cleaned, and dried, such as about 90° C. or below, such as about 70° C. or below, such as about −50° C. to about 60° C., such as about −40° C. to about 50° C., such as about −20° C. to about 30° C., such as about 0° C. to about 10° C. The composition of the reversible adhesive 204 is configured to release one or both of the minor component 206 and major component 202 when exposed to a predetermined condition. The predetermined condition can be a temperature, such as a temperature above a predetermined temperature, an electromagnetic energy exposure, a predetermined pH value, or combinations thereof depending on the composition of the reversible adhesive 204. The reversible adhesive 204 can be exposed to the predetermined condition for a predetermined time depending on the composition of the reversible adhesive 204. In some embodiments, the composition and conditions for assembling and disassembling the reversible adhesive 204 is the same for each minor component 206, or is different for two or more (e.g., each) minor component 206 located on a major component depending on the composition of the minor component 206. The difference in disassembly conditions is useful for separating different components sequentially. Separating different components sequentially enables ease of sorting of various different types of materials that are categorized into different recycle categories. In some embodiments, the reversible adhesive 204 composition is determined based on the composition of the major component 202. The reversible adhesive 204 composition includes a material that is compatible and capable of adhering to the composition of the major component 202.

Apparel Product Components

One or more of the apparel product components (e.g., 202, 204) can include different forms and compositions, such as animal-derived or plant-based natural fibers and compositions (e.g., cotton, linen, hemp, silk, cashmere, wool, jute, bamboo, leather), regenerated cellulose compositions (e.g., acetate), synthetic compositions (e.g., fibers, sheets, patches, liners, shells, woven, non-woven), and any material known in the apparel product industry. The apparel product components can include polymer materials, such as thermoplastic synthetic materials. The apparel product components can include one or more materials including polyester, such as polyethylene terephthalate (referred to herein as "PET"), acrylic, materials generated from cellulose (e.g., rayon, lyocell, viscose, modal, bamboo), cellulose acetate, polyamide (e.g., nylon), polyether-polyurea copolymer (e.g., elastane, spandex, Lycra®), polyurethane, neoprene, polyacetal, polypropylene, polyvinyl chloride (PVC), blends thereof, and combinations thereof. Other materials are also contemplated such a polybutylene terephthalate (referred to herein as "PBT") and polybutylene succinate (referred to herein as "PBS"). The apparel product components (e.g., 202, 204) can be formed using fibers, such as finely woven microfibers, filaments, yarns, or combinations thereof.

The apparel products having the apparel product components can be machine washable, machine dryable, hand washable, dry cleanable, or combinations thereof. In some embodiments, the apparel products are dry clean only or hand wash only. In some embodiments, the apparel products can have portions that are sewn together, or the apparel products can be free of sewn portions. Other forms and compositions of apparel product components are also contemplated, such as post-consumer plastic (PCP). In some embodiments, the composition of at least one of the apparel product components contains about 25 wt. % or less PCP material, such as about 1 wt. % to about 20 wt. %, such as about 2 wt. % to about 15 wt. %, such as about 4 wt. % to about 10 wt. %, such as about 6 wt. % to about 8 wt. %.

At least one of the one or more apparel product components (e.g., 202, 204) can be recyclable, such as at least two of the apparel product components. Each of the apparel product components can be the same recycle category or grade and can be recycled together. Alternatively, at least two of the apparel product components are categorized as different recycle categories or grades and recycled separately. Separating apparel product components from non-recyclable apparel product components and/or recyclable apparel products categorized as a different grade can be time consuming, expensive, or difficult due to the manner in which the components are coupled together. It has been discovered, that using a reversible adhesive 204 to join components together enables joining the apparel product components, such that the apparel products are wearable and durable for a variety of conditions without separation. As used herein, the term "recyclable material" refers to a material that can be processed and used again in new products, such as incorporated into new apparel products.

In some embodiments, one or more of the apparel product components have glass transition temperature ($T_g$) of about −20° C. to about 250° C., such as about −10° C. to about 200° C., such as 10° C. to about 100° C. In some embodiments, one or more of the apparel product have a melting temperature ($T_m$) of about 75° C. to about 200° C., such as 100° C. to about 175° C., such as about 125° C. to about 150° C.

In some embodiments, the reversible adhesive 204 includes particles 203 disposed therein. The particles 203 can be nanoparticles or microparticles. The particles 203 can have a diameter of about 1000 μm or less, such as about 20 μm to about 500 μm, such as about 50 μm to about 400 μm, such as about 100 μm to about 300 μm, such as about 150 μm to about 200 μm. In some embodiments, the particles 203 have a diameter of about 1 μm to about 10 μm, such as about 3 μm to about 5 μm. In some embodiments, the particles 203 have a largest dimension of about 3 nm to about 100 nm, such as about 5 nm to about 80 nm, such as about 20 nm to about 60 nm, such as about 30 nm to about 50 nm, or about 100 nm to about 200 nm, such as about 150 nm to about 175 nm. In some embodiments, the particles 203 are encapsulated in a polymer. In some embodiments, the particles 203 are encapsulated with a polymer that is the same or compatible (e.g., miscible) with one or more polymers of the reversible adhesive. The particles can be in the form of plates, fibers, or rod-like particulates distributed through the reversible adhesive. In some embodiments, the particles are granular, spherical, oblong, rod-shaped, or semi-spherical nanoparticles or macroparticles.

The particles are configured to absorb non-contact electromagnetic energy, such as eddy current induction heating and/or microwave by directing the energy to the reversible adhesive, where the particles absorb the radiation and convert it to thermal energy. The thermal energy is sufficient to break the covalent bonds of the reversible adhesive 204 and release the components 202, 204 from one another.

In some embodiments, the particles can be heated or energized to heat or energize the reversible adhesive locally to a temperature greater than the temperature of the components of the apparel product. In some embodiments, the particles can be heated using electromagnetic energy such as microwave, ultraviolet, infrared, blue light, or other forms of electromagnetic energy. In some embodiments the electromagnetic energy can include one or more of microwave (e.g., wavelength of about 1 mm to about 1 m), ultraviolet (e.g., wavelength of about 10 nm to about 400 nm), infrared (e.g., wavelength of about 750 nm to about 1 mm), visible (e.g., wavelength of about 400 nm to about 750 nm), such as blue light (e.g., wavelength of about 400 nm to about 500 nm), or other forms of electromagnetic energy. The particles can be suspended uniformly throughout reversible adhesive, or the particles can be embedded or doped into the reversible adhesive, such as a surface of the reversible adhesive. In some embodiments, the particles are pre-mixed in the reversible adhesive to provide a homogeneous distribution through the reversible adhesive.

The reversible adhesive can be selectively heated by using metal-containing particles 203 disposed within the reversible adhesive. The particles can be embedded in the reversible adhesive at a concentration that enables heat transfer to the adhesive at the temperature range at which the reversible bonds break. In some embodiments, the apparel product components are maintained intact, without degradation during the heat transfer from an external heat source to the particles and to the reversible adhesive. In some embodiments, the reversible adhesive includes particles, such as metal-containing particles, such as an iron containing material, such as iron oxide. In some embodiments, the particles include $Fe_3O_4$, $\gamma\text{-}Fe_2O_3$, metallic iron, copper, aluminum, silver, cobalt, nickel, FeN, FePt, FePd, or combinations thereof. In some embodiments, the particles generate heat when exposed to microwave energy, such as from a microwave reactor. In some embodiment, the particles are exposed to microwave energy having a frequency of about 915 MHz to about 5 GHz, such as about 2.45 GHz to about 4 GHz. In some embodiments, the reversible adhesive 204 includes metal-containing particles and the apparel product is free of any other metallic components such that other portions of the apparel product is not selectively heated as the particles are heated.

In some embodiments, the reversible adhesive includes a particle loading of about 0.01 wt. % to about 20 wt. %, such as about 0.05 wt. % to about 5 wt. %, such as about 1 wt. % to about 4 wt. %, such as about 2 wt. % to about 3 wt %, or about 6 wt. % to about 10 wt. %, such as about 7 wt. % to about 9 wt. %, or about 8 wt. % to about 15 wt. %, such as about 10 wt. % to about 13 wt. %.

In some embodiments, the particles produce heat when exposed to static ($H\ dc$) or alternating ($H\ ac$) magnetic fields. The temperature of the reversible adhesive is locally increased by induction from the heated particles. In some embodiments, the alternating magnetic field is applied at a frequency of about 200 kHz to about 1000 kHz, such as about 300 kHz to about 900 kHz, such as about 600 kHz to about 800 kHz and strength of about 2 kA/m to about 30 kA/m, such as about 6 kA/m to about 11 kA/m.

In some embodiments, the reversible adhesive is free of metallic particles, such as for apparel products containing metal components, such as metallic zippers or metallic buttons. In some embodiments, the reversible adhesive is free of metallic particles, such as for apparel products composed of material having a glass transition temperature above the deactivating temperature. In particular, the reversible adhesive can be heated to a temperature that breaks the bonds of the reversible adhesive, the temperature being lower than the glass transition temperature of the apparel product.

Alternatively, or additionally, the particles include shape memory materials configured to deform upon exposure to light or heat which is described in further detail relative to shape memory materials described herein.

Alternatively, or additionally, the particles are configured to illuminate upon activation, such as electrical activation which is described in further detail relative to shape memory materials described herein.

Assembly of Apparel Product Components

Figure 3:
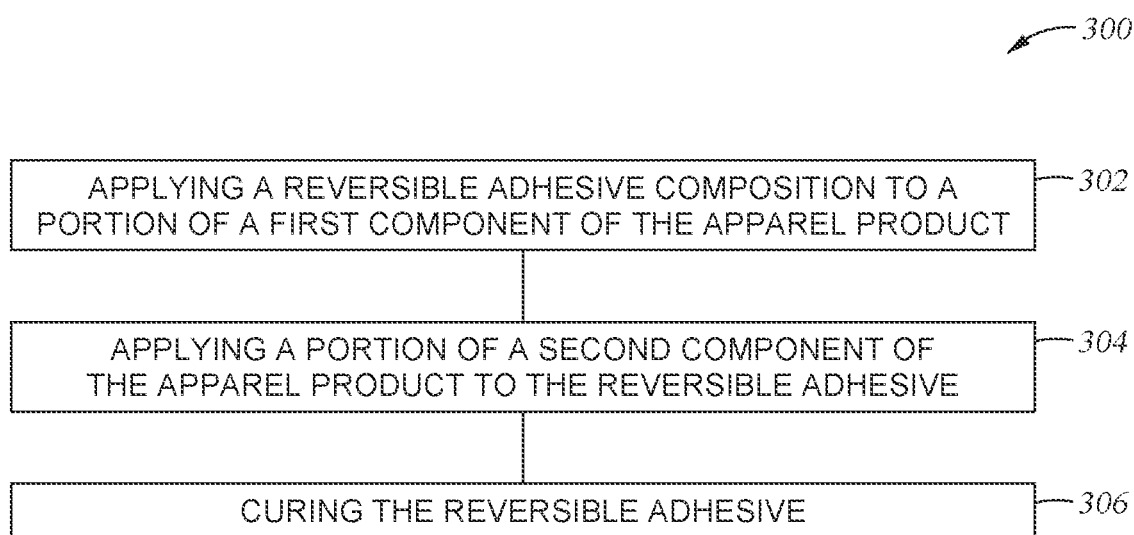
FIG. 3 depicts a process flow diagram of a method for assembling an apparel product according to some embodiments of the present disclosure.

FIG. 3 depicts a process flow diagram of a method 300 for assembling an apparel product according to some embodiments. The method 300 includes applying 302 a reversible adhesive composition to a portion of a first component of the apparel product, applying 304 a portion of a second component of the apparel product to the reversible adhesive, and optionally curing 306 the reversible adhesive. The reversible adhesive composition can be applied 302 using any method known in the industry depending on the composition of the reversible adhesive composition. In some embodiments, the reversible adhesive composition is applied by heat gun, printing, spraying, painting, dipping, roll on, screen printing, photolithography, transferring or spreading on by contact, or combinations thereof. The reversible adhesive composition can be in liquid form or a semiliquid gel form, or a foam when applied. In some embodiments, the reversible adhesive composition includes a foaming agent. The reversible adhesive composition can be crosslinked by applying a crosslinking condition, such as heat, electromagnetic energy, or combinations thereof. The crosslinking condition can be applied for a time of about 1 second to about 24 hours, such as about 5 seconds to about 2 hours, such as about 30 minutes to about 1 hour. Once the reaction for crosslinking occurs, the crosslinked reversible composition can be cured, such as by reducing the temperature.

Prior to use, the reversible composition can be stored in a kit, such as a two part kit and combined prior to applying to the components. Alternatively, the reversible adhesive composition is stored in a single container, such as a previously crosslinked reversible adhesive. The previously crosslinked reversible adhesive can be stored as strips or other geometries. In some embodiments, the previously crosslinked reversible adhesive can be treated by a deactivating condition prior to applying the adhesive/monomers thereof to the major component or minor component. The previously crosslinked reversible adhesive can be partially crosslinked or fully crosslinked. The storage container can include the reversible adhesive composition that has not yet been crosslinked. Overtime, the reversible adhesive composition can undergo partial bonding that increases the viscosity and changes dispensing properties such as flow rate of dispensing and component penetration. The bonding amount depends on time, temperature, and exposure to moisture. Although the term "applying" is used to describe transferring the reversible adhesive to the apparel product and pressing the components together, other terms can also be used such as coupling, transferring, contacting, pressing, or combinations thereof.

In some embodiments, such as for reversible adhesive with Diels-Alder bonds, to prevent issues with applying the reversible adhesive composition, the reversible adhesive composition, which can have partial bonding with a first viscosity and first molecular weight, can be pre-heated to a temperature of about 100° C. to about 200° C., such as about 150° C. for about 1 minute to about 30 minutes, such as about 5 minutes to about 20 minutes, such as about 10 minutes to about 15 minutes. After preheating, at least some of the partial bonds are broken and the reversible adhesive composition can have a second viscosity and second molecular weight. The second viscosity is less than the first viscosity and the second molecular weight is less than the first molecular weight. The viscosity is reduced to a predetermined viscosity that enables dispensing and/or spreading the reversible adhesive composition. After the reversible adhesive composition is dispensed between components or portions of components, the reversible adhesive composition can be allowed to bond by reducing a temperature of the reversible adhesive. For Diels-Alder, a bonding can occur at about 25° C. to about 100° C., such as about 70° C. for about 1 hour to about 7 days, such as about 1 hour to about 2 hours.

In some embodiments, components such as monomers are applied to the apparel product in one or more layers and the monomers react with one another once applied to the apparel product. In some embodiments, the monomers polymerize (e.g., cure) when applied to the apparel product. In some embodiments, the monomers do not react or react slowly until cured with a curing agent, thermal energy, electromagnetic energy, or combinations thereof. In some embodiments, the reversible adhesive is applied at a thickness of about 0.02 mm or greater, such as about 0.1 mm to about 5 mm, such as about 0.2 mm to about 3 mm, such about 0.3 mm to about 0.5 mm, or about 0.6 mm to about 0.8 mm. In some embodiments, the reversible adhesive can have a viscosity of about 1,000 cPs to about 10,000 cPs, such as about 3,000 cPs to about 6,000 cPs, such as about 3,500 cPs to about 5,000 cPs during application. In some embodiments, the reversible adhesive can be applied in a predetermined pattern on one or more components of the apparel product using photolithography, such as by curing by ultraviolet (UV) light.

Curing 306 the reversible adhesive can include any method known in the industry for curing adhesives, such as air drying, curing by applying heat, curing by applying electromagnetic energy, such as UV light, or combinations thereof. In some embodiments, the adhesive is solid upon curing. Prior to and/or during application, the removable adhesive can be maintained at a temperature of about 40° C. to about 200° C., such as about 80° C. to about 100° C. In some embodiments, curing 306 the reversible adhesive further includes applying a force to press the components against one another for a predetermined amount of time. A cure time can range from about 1 second to about 72 hours, such as about 1 hour to about 5 hours, such as about 1 minute to about 2 hours, such as about 10 minutes to about 30 minutes, or about 24 hours to about 48 hours. In some embodiments, curing includes exposure to ambient conditions, such as ambient air and humidity.

The method 300 is described in further detail relative to each adhesive composition described in further detail herein.

Disassembly of Apparel Product Components

Figure 4:
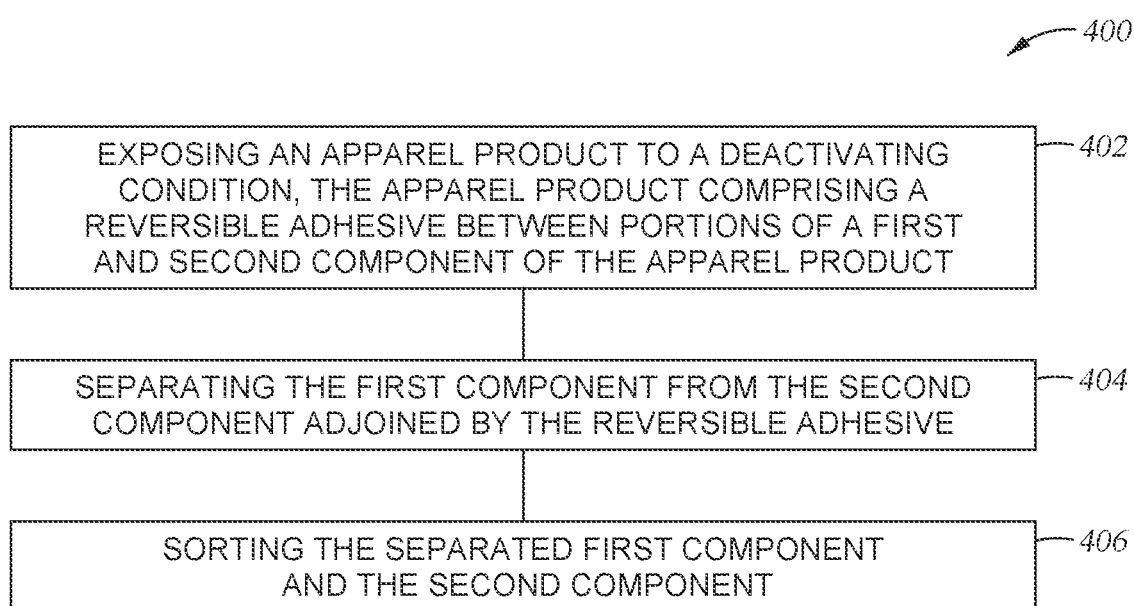
FIG. 4 depicts a process flow diagram of a method for disassembling an apparel product according to some embodiments of the present disclosure.

The reversible adhesive can be deactivated during disassembly of the apparel product under a predetermined condition depending on the composition of the reversible adhesive. FIG. 4 depicts a process flow diagram of a method 400 for disassembling an apparel product according to some embodiments. The method 400 includes exposing 402 an apparel product to a deactivating condition, the apparel product including a reversible adhesive between portions of a first and second component of the apparel product, separating 404 the first component from the second component adjoined by the reversible adhesive, and sorting 406 the separated components. In some embodiments, the reversible adhesive can include temperature reversible bonds, such as Diels-Alder bonds, chemical reversible bonds, such as disulfide bonds, thioester bonds, boronate bonds, imine bonds, light reversible bonds, such as cyclodextrin-azobenzene, shape memory materials, benzoxaborole bonds, oxime bonds, acylhydrazone bonds, thiol bonds, mixtures thereof, or combination(s) thereof. Other reversible bond types are also contemplated. In some embodiments, separating 404 further includes removing threads adjoining one or more components. Additionally, or alternatively, separating 404 further includes removing threads adjoining one or more portions of one or more components. The threads can be composed of a recyclable material or a non-recyclable material. In some embodiments, the threads are composed of nylon.

The deactivating condition can be a temperature, such as a temperature below a degrading temperature of the apparel product components and above a minimum deactivating temperature for deactivating the reversible adhesive. In some embodiments, the deactivating temperature of the reversible adhesive is about 100° C. to about 180° C., such as about 120° C. to about 160° C., such as about 130° C. to about 140° C. In some embodiments, a collection of apparel products are collected and heated in a process chamber, such as a furnace, a microwave oven, an electromagnetic oven, an induction oven, or other equipment known in the art configured to transfer heat selectively to the reversible adhesives without significantly heating the apparel material being separated.

The deactivating condition can be a predetermined pH change or a predetermined pH range. In some embodiments, the apparel products are exposed to the deactivating condition in one or more baths, such as one or more solvent baths having a controlled pH range, such as a basic solution, a caustic solution, or combinations thereof. Each of the one or more baths can be configured to mechanically agitate the apparel products, such as spinning in a washing machine. The reversible adhesive is exposed to the one or more baths and reverse the reversible adhesive. In some embodiments, the apparel products can be rinsed after exposure to the deactivating condition to remove monomers and other byproduct(s) of the reversed adhesive.

The deactivating condition can be an exposure to electromagnetic energy within a predetermined range of wavelengths. In some embodiments, the deactivating condition is an exposure to one or more of microwave (e.g., wavelength of about 1 mm to about 1 m), ultraviolet (e.g., wavelength of about 10 nm to about 400 nm), infrared (e.g., wavelength of about 750 nm to about 1 mm), visible (e.g., wavelength of about 400 nm to about 750 nm), such as blue light (e.g., wavelength of about 400 nm to about 500 nm), or other forms of electromagnetic energy. In some embodiments, a portion of the apparel producing including the reversible adhesive can be stretched to enable penetration of the deactivating condition to the reversible adhesive. In some embodiments, the portion including the reversible adhesive can be composed of a stretchable material, such as a material including spandex. Without being bound by theory, it is believed that stretching the fabric enables providing tension on the adhesive bonds and increasing an area of exposure to enable penetration of the electromagnetic energy, such as light to the reversible bonds.

Upon energizing the reversible adhesive, reversible bonds of the reversible adhesive are broken and the viscosity of the reversible adhesive is substantially reduced. In some embodiments, the reversible adhesive is soluble in a solution, such as water or in a solvent upon energizing the reversible adhesive. The broken reversible chemical bonds and reduced viscosity reduces the adhesive strength of the reversible adhesive. The portions of the components held together by the reversible adhesive can be separated (e.g., 404) by application of a force, such as pulling the components apart. In some embodiments, separating 404 includes separation by gravity or mechanical agitation, such as a tumble dryer, centrifugal separator, or other reactor. In some embodiments, operations 402 and 404 occur substantially simultaneously, such as in a tumble dryer with heating applied simultaneously with tumbling or other agitation. In some embodiments, the components are separated prior to introducing the separated components into a centrifuge. In some embodiments, the reversible adhesive is separated from the components in the centrifuge. In some embodiments, the reversible adhesive is dissolved in the centrifuge.

In some embodiments, such as in large scale separation, the apparel products can be placed in a process chamber configured to apply centrifugal force on the components of the apparel products to induce separation of the deactivated adhesives from the apparel components. The centrifugal force is configured to pull the depolymerized liquid adhesive (e.g., deactivated reversible adhesive) off the apparel products. In some embodiments, the process chamber is a high speed centrifuge that can be temperature and pressure controlled. In some embodiments, the apparel products can be processed in the device at a rotational speed of about 50 rpm or greater, such as about 100 rpm to about 150,000 rpm, such as about 500 rpm to about 1,000 rpm, such as about 1,500 to about 3,000 rpm, or about 4,000 rpm to about 5,000 rpm. The apparel products can be processed in the process chamber for about 10 seconds to about 48 hours, such as about 20 seconds to about 24 hours, such as about 30 seconds to about 16 hours, such as about 5 minutes to about 20 minutes, or about 30 minutes to about 1 hour, or about 2 hours to about 4 hours, or about 6 hours to about 8 hours. In some embodiments, the deactivated reversible adhesive can be spun out of a chamber volume of the process chamber. In some embodiments, each of the one or more components of the apparel products can be grouped within the process volume by product density or size. In some embodiments, the separated components are sorted by passing the components through one or more sieves. Small components such as buttons can pass through openings in the sieve and be separated from the bulk components. The one or more components can also be sorted by separating out buoyant components that float to the surface of a solution and/or non-buoyant components that sink to the bottom of a solution. In some embodiments, the components are disposed at different heights within a solution based on a density of the components. For example a density of a nylon can be about 1.0 g/cc, a density of polyester can be about 1.3 g/cc and a density of cotton can be 1.5 g/cc. Each of the nylon, polyester, and cotton can be separated from one another based on differences in density. In some embodiments, different components are sorted by differences in color using computer vision methods.

Sorting 406 the separate components can include categorizing the components by recycle groups to be recycled, reused, or discarded in accordance with the recycle group or category. In some embodiments, the reversible adhesive material can be collected, recycled, reused, discarded, or combinations thereof. In some embodiments, the components are separated based on material density, color, rheology, or other physical attribute. Once grouped, each of the components can be further rinsed or washed with a solvent, surfactant, or other solution to remove debris or residual reversible adhesive. Each group of components can be further characterized, such as by spectroscopy, chromatography (e.g., gel permeation chromatography), or other test method. The testing can determine the quality of the components and method for recycling the materials. Recycling can be done in any method known in the industry, such as by shredding, granulating, melting, extruding, pelletizing, or combinations thereof. After sorting the components by a first attribute, such as density, the components can be further separated based on additional attributes such as a second attribute, such as color.

Apparel products assembled with reversible adhesives described herein are disassembled by treating the reversible adhesive with a deactivating condition. The deactivating condition converts the reversible adhesive to a treated reversible adhesive with a reduced viscosity and/or reduced adhesive properties. The components coupled together by the reversible adhesives can be separated once the reversible adhesive is treated. The treated reversible adhesives can be removed from the components by a force, such as a centrifugal force in a spinner. Components of the apparel product can be sorted and separated by a physical attribute, such as by component density, which can be detected by difference in component buoyancy when suspended in a fluid. In addition to using buoyancy force to separate components of different densities, other methods are also contemplated such as near-infrared optical methods to differentiate components by component chemistry. The separated components can be further sorted by a second physical attribute such as color (e.g., pigment intensity).

In some embodiments, a large number of apparel products are mass processed. The apparel product components are first spread apart onto a surface, such as a conveyor belt. Arranging the apparel product components can include running a conveyor belt at a speed below a container of numerous apparel components. At the bottom of the container, a dispenser opens and closes at a frequency to drop a small number of apparel product components onto the conveyor belt. The speed of the conveyor belt, the size of the opening of the dispenser at the bottom of the container, and a cycle time of the dispenser opening and closing are tuned to control the amount of the components in each group and how far apart the components are distributed along the conveyor belt. When the apparel product components travel on the conveyor belts in small groups, mechanical grippers with long and slender tips are used to pinch and pick up individual components. The grippers can be guided by a computer vision algorithm with the ability to detect an attribute such as color.

Reversible Adhesive Backbone

As used herein, the term "backbone" refers to a polymer structure that can be further functionalized with functional groups to form the bonds described in more detail herein, such as Diels-Alder bonds, disulfide bonds, thioester bonds, boronic acid bonds, imine bonds, cyclodextrin-azobenzene bonds, shape memory materials, or combinations thereof. The reversible adhesive backbone can include one or more monomers (as reacted monomeric units) that have been polymerized or copolymerized. In some embodiments, the reversible adhesive includes monomeric units of acrylate, methacrylate, acrylic, ethylene, propylene, styrene, vinyl acetate, vinyl ester monomers, or combinations thereof.

The reversible adhesive can include acrylic monomeric units, such as acrylic acid (AA), methacrylic acid (MAA), esters of AA and MAA, itaconic acid (IA), crotonic acid (CA), acrylamide (AM), methacrylamide (MAM), and derivatives of AM and MAM, e.g., alkyl (meth)acrylamides. Esters of AA and MAA include alkyl, hydroxyalkyl, phosphoalkyl and sulfoalkyl esters, e.g., methyl methacrylate (MMA), ethyl methacrylate (EMA), butyl methacrylate (BMA), hydroxyethyl methacrylate (HEMA), hydroxyethyl acrylate (HEA), hydroxypropyl methacrylate (HPMA), hydroxybutyl acrylate (HBA), methyl acrylate (MA), ethyl acrylate (EA), butyl acrylate (BA), 2-ethylhexyl acrylate (EHA), cyclohexyl methacrylate (CHMA), benzyl acrylate (BzA), isooctyl acrylate, lauryl acrylate, stearyl acrylate, and phosphoalkyl methacrylates (e.g., PEM). In some embodiments, the backbone polymer can further include gel compositions, such as polyethylene glycols (PEG), poly(2-oxazoline), poly(2-oxazine), derivatives thereof, and mixtures thereof.

In addition to the backbone polymer, any of the reversible adhesives described herein can further include additional additives or polymers, such as tackifiers, antioxidants, nucleators, energy absorbers, curing agents, or combinations thereof. In some embodiments, these additional additives or polymers can be present in the reversible adhesive in an amount of about 1 wt. % to about 40 wt. %, such as about 5 wt. % to about 30 wt. %, such as about 10 wt. % to about 20 wt. %.

The reversible adhesives have adhesive properties suitable to withstand normal use, cleaning, and drying of the apparel products. In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015). As used herein, adhesive strength, such as T-peel can be measured using any test methods known in the industry.

Moreover, adhesive strength can depend on the adhesive, the mechanical strength of the component, the mechanical strength of the adjoined structure, the type of adjoined structure, or combinations thereof. The adjoined structure can be a butterfly joint or an overlap joint.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

In some embodiments, the reversible adhesive includes multiple layers such as a primer layer disposed between the component of the apparel product and an adhesive layer that includes the reversible bonds.

The reversible adhesives described herein are different from conventional adhesives, such as adhesives that melt with no bonds being broken. Without being bound by theory, the crosslinking covalent bonds described herein provide adhesive strength and an ability to bond to the materials of the apparel product components. It is believed that when disassembly conditions are met, these bonds will break and cause the reversible adhesive to lose strength and tackiness. The breaking of the bonds enable complete separation between the adhesive and the apparel material in a chemical process. Additionally, the molecular weight of the reversible adhesive before breaking the bonds (e.g., can be up to infinite molecular weight) is higher than the molecular weight of the reversible adhesive after breaking the bonds.

In contrast, conventional thermoplastic adhesives do not contain crosslinking bonds. When heated, conventional adhesives become softer and easier to flow because of increased chain mobility and little or no covalent bonds are broken. The molecular weight of the conventional adhesive remains substantially the same before and after heating the adhesive, which would otherwise make any disassembly very difficult. The heated conventional adhesive remains viscous and tacky due to the high molecular weight. As a result, the two substrates being bonded by the conventional adhesive may be separated but it is difficult to separate the adhesive from the substrates. The melting of thermoplastic adhesives is a physical process rather than a chemical process described relative to the reversible adhesives described herein.

Cycloalkene Bonding

In some embodiments, the reversible adhesive includes thermoreversible bonds, such as cycloalkene bonds, such as cyclo-monoalkene bond. The cycloalkene bonds can be part of a polymer network such as any of the backbone polymers described herein. In some embodiments, the polymer network includes a polyester, polypropylene, polyethylene, poly(ester urethane), copolymers thereof, or combinations thereof. The cycloalkene bonds, also referred to herein as "Diels-Alder" bonds can be formed between various diene and dienophile groups, such as maleimide and furan groups, such as bis-maleimide and trifunctional furan. The diene and dienophile composition can be selected such that a temperature used to reverse the reversible adhesive can be controlled to be within a predetermined temperature, such as below the temperature at which the components degrade and above a temperature the apparel product can be worn, used, cleaned, and dried. The diene and dienophile group ratios can be selected to obtain reversible adhesive having different properties, such as cross-linking densities. In some embodiments, the reversible adhesive is doped with Diels-Alder functional groups. In some embodiments, the copolymer functionalized with diene includes furfuryl methacrylate. In some embodiments, the diene copolymer, such as furfuryl methacrylate is present in the reversible adhesive in an amount 10 wt. % to 99 wt. %, such as about 20 wt. % to about 80 wt. %, such as about 20 wt. % to about 30 wt. %, based on the weight of the reversible adhesive.

In some embodiments, adducts form between the diene and dienophile groups at a temperature of about 80° C. or lower, such as about 20° C. to about 80° C., such as about 30° C. to about 70° C. In some embodiments, the adducts are formed after about 1 minute to about 2 hours at the temperature, such as about 5 minutes to about 1 hour, such as about 10 minutes to about 30 minutes. The reversible adhesive including the adducts include cross-linked bonds having bond strengths and bonds with suitable adhesion properties for apparel products. The adducts can be debonded (reversible bond) at temperatures of about 80° C. or greater, such as about 90° C. to about 200° C., such as about 100° C. to about 120° C., such as about 140° C. to about 160° C. The cross-linked bonds of the molecular structure of the reversible adhesive can break, resulting in lower molecular weight and low modulus as well as reduced viscosity and increased solubility in a solvent. As used herein, a "solvent" refers to an organic solvent such as an aliphatic solvent, aromatic solvent, an alcohol solvent, a glycol ether solvent, or combinations thereof. In some embodiments, a solvent is selected depending on the polymer backbone used for a polymer of the adhesive. A force, such as a centrifugal force of a device can separate components that are joined together by the reversible adhesive and the reversible adhesive from the components once the reversible adhesive bond is broken. In some embodiments, the apparel product can be heated while being rotated in a centrifuge at a temperature that can break the Diels-Alder bonds.

The reversible adhesive can be prepared by forming a polyketone. The polyketone can include carbon monoxide, propylene, ethylene, or a combination thereof. In some embodiments, the propylene to ethylene weight ratio is about 1:0 to about 10:1, such as about 1:1 to about 5:1, such as about 2:1 to about 4:1. The polyketone can be grafted with furfurylamine. The grafted polyketone can be at least partially functionalized with furan groups and crosslinked with bismaleimide.

Bismaleimide resins can include, but are not limited to, bis(3-ethyl-5-methyl-4-maleimidophenyl)methane, 4,4'-bis-maleimido-diphenylmethane, 1,4-bismaleimido-2-methyl-benzene and mixtures thereof; modified and partially advanced modified bismaleimide resins containing Diels- Alder comonomers; and a partially advanced bismaleimide based on 4,4'-bismaleimido-diphenylmethane and allylphenyl compounds or aromatic amines. In some embodiments, the bismaleimides useful for the reversible adhesives described herein include a bismalemide having about 2 to about 100 carbons, such as long-chained branched 36-carbon bismaleimide.

Suitable Diels-Alder dienophiles include styrene and styrene derivatives, bis(propenylphenoxy) compounds, 4,4'-bis(propenylphenoxy)sulfones, 4,4'-bis(propenylphenoxy)benzophenones, 4,4'441-methyl ethylidene), bis(2-(2-propenyl) phenol), Bis(3-ethyl-5-methyl-4maleimidophenyl)methane, 1,4-Di(maleimido) butane, N,N'-(1,3-Phenylene)dimaleimide, N,N'-(1,4-Phenylene)dimaleimide, N,N'-(o-Phenylene) dimaleimide, and 1,1'-(Methylenedi-4,1-phenylene)bismaleimide.

Bismaleimides (dienophiles) can be based on 4,4'-bismaleimido-diphenylmethane and an allylphenyl compound, such as diallylbisphenol-A. Other bismaleimides can include a nucleophilic addition of a nucleophile (or a carbanion) to an α,-unsaturated carbonyl compound including copolymers of bismaleimide and aromatic diamines, such as 4,4'-bismaleimido-diphenylmethane/4,4'-diaminodiphenylmethane. In some embodiments, bismaleimide resins are based on 4,4'-bismaleimido-diphenylmethane. Alternative crosslinking agents (dienophiles) may include acetylenes and thioesters substituted with an electron-withdrawing group.

The amount of bismaleimide can be controlled to achieve a predetermined crosslinking density. In some embodiments, the diene group to dienophile molar ratio, such as furan group to maleimide molar ratio, is about 5:1 to about 1:1, such as about 4:1 to about 2:1, such as about 3:1. In some embodiments, the furfuryl moiety to bismaleimide molar ratio is about 2:1 to about 1:2, such as about 1:1 to about 2:3.

Without being bound by theory, it is believed that reversible adhesives including higher dienophile to diene molar ratios are considered to have lower network mobility and require higher temperatures for crosslink bonds to break. Depending on the apparel product material considerations, a temperature range at which Diels-Alder bonds break is selected and tuned by controlling a molar ratio of dienophile to diene. Controlling a temperature range at which the reverse reaction occurs enables preventing premature degradation of apparel products during normal use, cleaning, and overall life of apparel products.

Additionally, it is further believed that the temperature range at which the reverse reaction occurs can be controlled by adjusting relative amounts of monomers that make up the polymer backbone of the adhesive. In some embodiments, increasing an ethylene content, such as to an amount of about 20 wt. % to about 50 wt. % ethylene of total weight of ethylene and propylene used for the polymerization reaction, can increase a temperature range at which the reverse reaction occurs relative to propylene backbone adhesives that do not include ethylene. Lower network mobility can also lead to longer times to break the bonds. Thus, monomer content and dienophile to diene molar ratio can be controlled to enable a suitable time to disassemble the apparel products, such as about 10 seconds to about 5 hours, such as about 30 seconds to about 1 hour, such as about 1 minute to about 30 minutes.

The reversible adhesive can be heated to the temperature range at which the reversible bonds break, while maintaining a temperature of the surrounding materials to prevent degradation of the other components of the apparel products or the debonding of another reversible adhesive designed to be debonded at a different condition to further separate additional components sequentially. The reversible adhesives are particularly advantageous with the particles 203 described relative to FIG. 2.

In some embodiments, the reversible adhesive includes a monomer including a diene, such as a diene acrylate or methacrylate and a dienophile, such as a bismaleimide crosslinking agent.

In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015).

In some embodiments, the reversible adhesive with Diels-Alder bonds have a bond strength of about 4 mPa to about 12 mPa, such as about 5 mPa to about 10 mPa, such as about 5 mPa to about 8 mPa at 23° C. when bonded to a major and/or minor component described herein. In some embodiments, the reversible adhesive with Diels-Alder bonds have a bond strength of about 0.25 mPa to about 4 mPa, such as about 0.5 mPa to about 3 mPa, such as about 1 mPa to about 2 mPa at 80° C. when bonded to a major and/or minor component described herein.

In some embodiments, the reversible adhesive has a modulus of about 3 mPa to about 3500 MPa, such as about 10 mPa to about 3000 MPa, such as about 50 mPa to about 1500 mPa, such as about 90 mPa to about 125 mPa, according to tensiometric analysis using 100 N force and rate of 100 mm/min. In some embodiments, prior to crosslinking a polymer to form the reversible adhesive, the polymer has a glass transition temperature ($T_g$) of about −20° C. to about 200° C., such as about −10° C. to about 100° C., such as about 10° C. to about 20° C. In some embodiments, prior to crosslinking a polymer to form the reversible adhesive, the polymer has a melting temperature ($T_m$) of about 75° C. to about 200° C., such as 100° C. to about 175° C., such as about 125° C. to about 150° C. As used herein, unless otherwise indicated, the term "modulus" refers to tensile modulus which is measured using a method based on ASTM D412 for materials having a modulus between 3 MPa to about 100 MPa or based on ASTM D638 for materials having a modulus from about 100M Pa to 3500 MPa.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

In some embodiments, the reversible adhesive includes about 70 wt. % to about 85 wt. % 2-ethylhexyl acrylate (EHA), about 3 wt. % to about 15 wt. % ethyl acrylate (EA), about 2 wt. % to about 10 wt. % methyl methacrylate (MMA), about 0 wt. % to about 7 wt. % furfuryl methacrylate (FFMA), about 1 wt. % to about 7 wt. % acrylic acid (AA), and about 0.1 wt. % to about 1 wt. % n-dodecyl mercaptan (n-DDM).

Thioester Bonding

In some embodiments, the reversible adhesive includes pH reversible adhesives, such as reversible bonds produced by reversible covalent linkages, such as a linkage formed between an electrophilic moiety and a nucleophilic moiety. In some embodiments, reversible covalent linkages, such as thioester linkages can be formed from reacting an electrophilic moiety or electrophilic compound and a nucleophilic moiety or nucleophilic compound, such as thiol. The electrophilic moiety or electrophilic compound can include an acrylamide, alkyl halide, alkyl sulfonate, aziridine, epoxide, haloacetamide, maleimide, sulfonate ester, acid halide, carboxylic acid, acrylate, methacrylate, pentafluorophenyl groups, or combinations thereof. The electrophilic moiety containing materials can be selected based on the backbone material and the predetermined conditions (e.g. pH range) for reversing the reversible adhesive.

Thioester linkages can be formed as part of thioester exchange reactions, such as thiol-thioester exchanges. A thiol-thioester exchange includes a thiolate anion reaction with a thioester to form thiolate and thioester products. Thioesters can also hydrolyze in water to form carboxylic acids. The relative rates of exchange and hydrolysis are competing reactions that can be controlled by exposing the reactants to a solution with a predetermined pH to aid the desired reaction such as a reaction that favors or limits hydrolysis over thiol-thioester exchange. Hydrolysis is typically considered an unstable state. In some embodiments, the reversible adhesive includes one or more of the materials such as polymers described relative to thermoreversible adhesives. The reversible adhesive contains a reaction product of thiol-thioester reactants.

The reversible adhesive can be formed and is stable when exposed to solutions with a pH of about 3 to about 8, such as about a pH of about 4 to about 7, such as about 5 to about 6. In some embodiments, the reversible thiol-thioester exchange reaction can occur at ambient conditions. In some embodiments, the reversible adhesives are cured by exposure to UV radiation. In some embodiments, the reversible adhesives can be reversed by exposure to UV radiation.

The reversible adhesive can be formed by combining a first crosslinkable polymer having thiol moieties and a second crosslinkable polymer having electrophilic crosslinkable moieties. The crosslinkable moieties of the second crosslinkable polymer are capable of reacting with the thiol moieties of the first crosslinkable polymer to form thioester linkages between the first and second crosslinkable polymers. The first crosslinkable polymer can further include additional moieties such as thioester, alcohol, amine, and combinations thereof. In some embodiments, a reversible adhesive copolymer that contains an adhesive component such as butyl acrylate and a crosslinkable component such as poly(thiophenyl methacrylate) can be reacted with a bisthiol (i.e. 1,4 dithiobutane) or a bisamine (cysteamine dihydrochloride) to provide crosslinking. For crosslinking with a bisthiol, reversing the crosslinking would be based on the hydrolysis of thioesters. For crosslinking with a cysteamine the disulfide bond is the reversible bond.

The reversible adhesive can be formed by combining a first crosslinkable polymer having thioester moieties and a second crosslinkable polymer having crosslinkable moieties. The crosslinkable moieties of the second crosslinkable polymer are capable of reacting with the thioester moieties of the first crosslinkable polymer to form thioester linkages between the first and second crosslinkable polymers. The first crosslinkable polymer can further include additional moieties such as thiol, alcohol, amine, and combinations thereof. As used herein, a "thioester" is a compound having the formula R—S—CO—R', where R and R' are, independently carbon and/or hydrogen containing groups having 1 to about 29 carbons, such as about 2 to about 20 carbons, such as about 5 to about 10 carbon atoms. As used herein, a "thiol" is a compound having the formula R—SH, where R is a carbon and/or hydrogen containing group. As used herein a "unit" is a monomeric unit that is part of a polymer of the present disclosure.

Table I lists several non-limiting examples of thioesters and thiols that can be used to form the reversible adhesives described herein.

TABLE 1

Example Thiols and Thioesters

| Thioesters | Thiols |
|---|---|
| 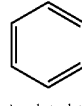<br>Acylated thiophenol | 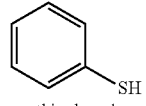<br>thiophenol |
| 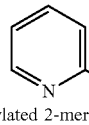<br>Acylated 2-mercaptopyridine | 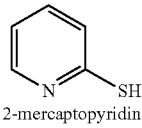<br>2-mercaptopyridine |
| n-oct-SAc<br>Acylated 1-octanethiol | n-oct-SH<br>1-octanethiol |
| 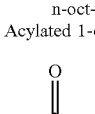<br>Acylated methyl 3-mercaptopropionate | 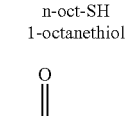<br>methyl 3-mercaptopropionate |
| 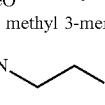 Acylated<br>2-(boc-amino)ethanethiol<br>Boc = tert-butyloxycarbonyl | 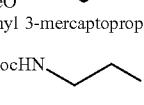<br>2-(boc-amino)ethanethiol<br>Boc = tert-butyloxycarbonyl |

The reversible adhesive can include a first crosslinkable polymer having activated esters (e.g., N-hydroxysuccinimide) and a second crosslinkable polymer having thiol moieties functionalized to the backbone or formed as part of the backbone.

In some embodiments, the reversible adhesive is reversed by exposing the reversible adhesive to a solution. The solution can have a pH below 3 or above 8. In some embodiments, the reversible adhesive degrades and the components held together by the reversible adhesive can be separated at pH levels below 3, such as about 1 to about 2.9, such as about 1.4 to about 2.8, such as about 1.6 to about 2.6, In some embodiments, at pH levels above 8 pH, such as about 8.1 to about 14, such as about 9 to about 13, such as about 10 to about 12, the reversible adhesive degrades and the components held together by the reversible adhesive can be separated. The degradation of the reversible adhesive includes hydrolyzing the thiol-thioester. The material of the apparel product components are maintained without degradation. In some embodiments, thioesters having a $pK_a$ of about 2 to about 8 $pK_a$ reacts with thiols with a $pK_a$ of about 2 to about 10 $pK_a$. In some embodiments, the solution can include solvents, such as dimethylformamide, dimethylsulfoxide, acetone, ethyl acetate, toluene, or chloroform. The pH of the solution can be adjusted using a nucleophilic catalyst, such as an amine catalyst, such as dimethylaminopyridine, 1,4-diazabicyclo[2.2.2]octane, quinuclidine.

In some embodiments, the solution includes a thiolate compound. The thiolate compound can include a linear, branched and/or dendritic multi-thiol macromolecule, poly (ethylene glycol) thiol, thiol containing glycerol, thiol containing peptide, cysteine, cystine, alkyl ester of cysteine, alkyl ester of cystine, $MeSCH_2SH$, (R)/(S)-3-methyl-3-sulfanylhexan-1-ol, ethanethiol, 1-propanethiol, 2-propanethiol, butanethiol, tert-butyl mercaptan, pentanethiols, thiophenol, dimercaptosuccinic acid, thioacetic acid, 5-mercapto-4H-[1,2,4]triazol-3-ol, 2-mercaptoacetamide, 2-mercaptoethanol, 1,2-ethanedithiol, ammonium thioglycolate, cysteamine, methyl thioglycolate, thiolactic acid, 1-mercapto-2-propanol, 2-methoxyethanethiol, 3-mercapto-1-propanol, 2,3-dimercapto-1-propanol, 1-thioglycerol, mercaptosuccinic acid, 4-ethyl-5-mercapto-4H-1,2,4-triazol-3-ol, N-carbamoyl-L-cysteine, 2-methyl-3-sulfanylpropanoic acid, 4-mercaptobutyric acid, N-acetylcysteamine, 3-methyl-1-butanethiol, 1,5-pentanedithiol, 4-chlorothiophenol, 4-aminothiophenol, benzyl mercaptan, 2-furanmethanethiol, 3-mercaptohexanol, furfuryl thiol, derivatives thereof, a disulfide complex of one or more thereof, and any combinations thereof.

Without being bound by theory, it is believed that the thio-thioester exchange reaction between the thioester linkages in the reversible adhesive and the thios of the thiolate compound leads to dissolution of the reversible adhesive.

In some embodiments, a plurality of apparel products that include the reversible adhesive can be soaked in the solution and agitated. In some embodiments, the plurality of apparel products can be soaked in a first solution having a first pH, then soaked in a second solution having a second pH. In some embodiments, the first pH can be less than 3 pH and the second pH can be greater than 8 pH. In some embodiments, the first pH can be greater than 8 pH and the second pH can be less than 3 pH. In some embodiments, the apparel product can be rinsed after the first soak and/or rinsed after the second soak. The reversible adhesive formation and reversal can occur at ambient conditions, such as a temperature of about 16° C. to about 35° C., such as about 18° C. to about 26° C.

In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015).

In some embodiments, the reversible adhesive has a modulus of about 3 mPa to about 3500 MPa, such as about 10 mPa to about 3000 MPa, such as about 50 mPa to about 1500 mPa, such as about 90 mPa to about 125 mPa, according to tensiometric analysis using 100 N force and rate of 100 mm/min. In some embodiments, prior to crosslinking a polymer to form the reversible adhesive, the polymer has a glass transition temperature ($T_g$) of about −20° C. to about 200° C., such as about −10° C. to about 100° C., such as 10° C. to about 20° C. In some embodiments, prior to crosslinking a polymer to form the reversible adhesive, the polymer has a melting temperature ($T_m$) of about 75° C. to about 200° C., such as 100° C. to about 175° C., such as about 125° C. to about 150° C.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

In some embodiments, the reversible adhesive includes a copolymer of poly(thiomethacrylate)-r-(oligo(ethylene glycol)methacrylate). The oligo(ethylene glycol)methacrylate (OEGMA) component provides a water soluble component and the thiomethacrylate component can provide the crosslinkable group. In some embodiments, the reversible adhesive is a reaction product of a thioester having the formula below. The thioester can be bonded to any of the thiols described herein.

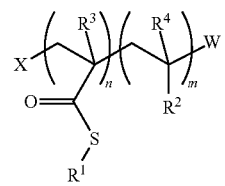

$R^1$ is a hydrogen, a linear hydrocarbon, a cyclic hydrocarbon, or a branched hydrocarbon, such as an alkyl or aromatic group. $R^2$ is a carboxyl group or a carbonyl group substituted with a linear hydrocarbon, a cyclic hydrocarbon, a branched hydrocarbon, or an ether group. In some embodiments, $R^2$ promotes solubility of the polymer in a solvent, such as an organic solvent, or in an inorganic solvent, such as water. In some embodiments, $R^2$ is a methacrylate or acrylate. $R^3$ and $R^4$ are each independently hydrogen, a linear hydrocarbon, a cyclic hydrocarbon, or a branched hydrocarbon, such as a methyl or ethyl group. X and W are each independently hydrogen, a linear hydrocarbon, a cyclic hydrocarbon, or a branched hydrocarbon, such as an alkyl or aromatic group. Each of "n" and "m" are independently a number from 1 to 1000, such as 100 to 800.

In some embodiments, the reversible adhesive is a reaction product of a thioester having the formula below.

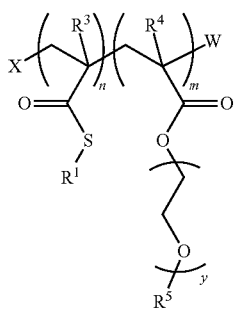

$R^1$ is a hydrogen, a linear hydrocarbon, a cyclic hydrocarbon, or a branched hydrocarbon, such as an alkyl or aromatic group. $R^3$, $R^4$, and $R^5$ are each independently a hydrogen, a linear hydrocarbon, a cyclic hydrocarbon, or a branched hydrocarbon, such as a methyl or ethyl group. X and W are each independently a hydrogen, a linear hydrocarbon, a cyclic hydrocarbon, or a branched hydrocarbon, such as an alkyl or aromatic group. Each of "n," "m," and "y" are independently a number from 0 to 1000, such as 100 to 800.

Disulfide Bonding

In some embodiments, the reversible adhesive includes pH reversible adhesives, such as reversible bonds produced by disulfide bonds. In some embodiments, the disulfide bonds are formed using any of the reversible adhesive backbone materials described herein, such as acrylic, methacrylic, derivatives thereof, or combinations thereof. In some embodiments, the reversible adhesive is a reaction product of a monomer including a sulfhydryl (thiol) group and oxidizing agents, such as iodine and oxygen-containing materials, such as sodium periodate, air, diatomic oxygen, 3,3'-dithiopropionic acid, gluthathione disulphide, or combinations thereof. The thiol groups can be any of the thiol groups described above with respect to thiols and can be converted to disulfide bonds by oxidizing the monomer. In some embodiments, the monomer including the thiol group is a reaction product of an amine containing monomer and 2-iminothiolate. In some embodiments, forming the disulfide bond is catalyzed with a disulfide derivative, such as pyridyl disulfide or 5-thio-2-nitrobenzoic acid.

In some embodiments, the reversible adhesive is formed by co-polymerization of N,N'-bis-acryloylcystamine with acrylamide in water to obtain disulfide-containing poly(acrylamide). The disulfide-containing poly(acrylamide) is formed by oxidation using a low molecular weight disulfide such as cysteamine, 2-hydroxyethyl disulfide, 3,3'-dithiodipropionic acid, or glutathione disulfide. In some embodiments, the reversible bond is reversed using dithiothreitol, glutathione, I-cysteine, or combinations thereof. In some embodiments, the disulfide-containing poly(acrylamide) is incorporated into other polymer networks including the backbone polymers described herein.

The reversible adhesive can be formed at a pH range of about 5 pH to about 11 pH, such as about 6 to about 10, such as about 7 to 9. In some embodiments, the reversible adhesive bonds can include additional polymers including other pH sensitive bonds, such as thiol groups or other pH sensitive groups described herein. Other pH sensitive bonds that can be included in polymers of the reversible adhesive include ketals that are labile in acidic environments, acetals, imines or iminiums, silicon-oxygen-carbon linkages, silicon-nitrogen linkages, such as silazanes, silicon-carbon linkages, such as arylsilane, vinylsilanes, and allylsilanes, bonds formed from maleic anhydride derivatives and amines, ortho esters, hydrazones, activated carboxylic acid derivatives, and combinations thereof.

Without being bound by theory, it is believed that a rate of oxidation of thiol, such as in air, can depend on pH. The oxidation can proceed generally in the following general mechanism.

$$R-SH + H_2O \rightleftharpoons R-S^- + H_3O^+$$

$$R-S^- + O \rightleftharpoons R-S^{\cdot} + O_2^-$$

$$2R-S^{\cdot} \rightarrow R-S-S-R$$

R is an atom or molecule containing carbon, hydrogen, or combinations thereof. In some embodiments, the rate of disulfide formation can be increased by increasing a concentration of free radicals, such as by introducing the reactants to ammonium persulfate and tetramethylethyldiamine.

In some embodiments, the reversible adhesive includes a disulfide-containing polyester. In some embodiments, the reversible adhesive can be cured by exposure to UV radiation. In some embodiments, the molecular weight distribution of the reversible adhesive is broadened by increasing a time of exposure to the UV radiation.

The reversible adhesive can be reversed by altering the pH outside of the formation range. Without being bound by theory, it is believed that a change in pH alters a solubility of the polymer having the disulfide bonds. In some embodiments, the apparel products having the reversible bonds can be submerged in a solution having a pH outside of the pH range at which the reversible adhesive is formed, such as about 1 pH to about 6 pH, such as about 2 pH to about 5 pH, such as about 3 pH to about 4 pH. The reversible adhesive can be reversed at pH below 6 or a pH above 7, such as a pH of about 1 to 2, or about 2 to about 3, or about 3 to about 4, or about 7 to about 8, or about 8 to 9, or about 9 to 10, or about 11 to 12, or about 12 to about 13, or about 13 to about 14. The pH of the solution can be tuned, altered, or buffered by adding one or more of carboxylic acids, imidazole, pyridine, phenols, polyamines, or combinations thereof. The reversible adhesive formation and reversal can occur at ambient conditions, such as a temperature of about 16° C. to about 35° C., such as about 18° C. to about 26° C. In some embodiments, the apparel product is submerged for about 1 second to about 24 hours, such as about 10 seconds to about 10 minutes, such as about 30 seconds to about 50 minutes, or about 20 minutes to about 3 hours.

Alternatively, or additionally, the reversible adhesive having disulfide bonds can be reversed by using reducing agents such as glutathione, 1-cysteine, or combinations thereof. Alternatively, or additionally, the reversible adhesive having disulfide bonds can be reversed using any of the thiols described herein. In some embodiments, the reversible adhesive having disulfide bonds can be reversed using monothiols, dithiols, phosphines, and combinations thereof.

In some embodiments, disulfide moieties include cystamine, cystin, N,N'-bisacryloyl-cystamine, or combinations thereof. In some embodiments, disulfide moieties can be introduced into a polymeric network simultaneously with radical polymerization.

In some embodiments, the reversible adhesive includes gels such as poly(ethylene glycol-block-propylene glycol-block-ethylene glycol) copolymers. In some embodiments, the reversible adhesive includes compositions having a structure:

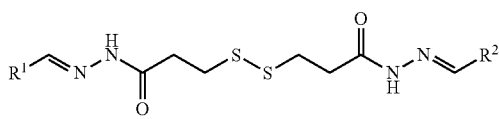

$R^1$ and $R^2$ are each independently hydrogen, linear hydrocarbon, branched hydrocarbon, or cyclic hydrocarbon. In some embodiments, $R^1$ and $R^2$ are each a polymer having the same type of monomeric units. In some embodiments, $R^1$ and $R^2$ are each a polymer having the different type of monomeric units. Each of the polymers are selected based on solubility in a predetermined solvent or other physical properties.

Without being bound by theory, it is believed that the disulfide group can be inserted to any polymer backbone structure between crosslinking bonds. In some embodiments, at least one of the cross-linked polymers being crosslinked is soluble in a solvent.

In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015).

In some embodiments, the reversible adhesive has a modulus of about 3 mPa to about 3500 MPa, such as about 10 mPa to about 3000 MPa, such as about 50 mPa to about 1500 mPa, such as about 90 mPa to about 125 mPa, according to tensiometric analysis using 100 N force and rate of 100 mm/min. In some embodiments, prior to crosslinking a polymer to form the reversible adhesive, the polymer has a glass transition temperature ($T_g$) of about −20° C. to about 200° C., such as about −10° C. to about 100° C., such as 10° C. to about 20° C. In some embodiments, prior to crosslinking a polymer to form the reversible adhesive, the polymer has a melting temperature ($T_m$) of about 75° C. to about 200° C., such as 100° C. to about 175° C., such as about 125° C. to about 150° C.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

Boronate Bonding

In some embodiments, the reversible adhesive includes reversible covalent bonds produced by reversible Lewis acid and Lewis base interactions. In some embodiments the Lewis acid can include monomers with boronic acid moieties, such as a phenylboronic acid. The Lewis acid can be crosslinked with monomers having other moieties (e.g., Lewis base). The other moieties can include diols. In some embodiments, the other moieties include amine, catechol, silanol, fructose, glucose, galactose, sorbitol, and combinations thereof. In some embodiments, the covalent bonds are formed between boron and oxygen, such as boronate ester bonds, such as cyclic boronic esters (e.g., 5, 6, or 7 member rings). In some embodiments, the covalent bonds are formed between boron and nitrogen.

In some embodiments, the monomers include two or more boronic acid moieties. The boronic acid moieties are attached to aromatic rings. The aromatic rings to which the boronic acid moieties are attached may be substituted with additional functional groups. In some embodiments, one or more aromatic rings are substituted with an electron withdrawing group, such as a nitro group (—$NO_2$). The two or more boronic acid moieties may be attached to the same aromatic ring, as for example, in 1,3-benzenediboronic acid (BDBA), or the boronic acid moieties may be attached to different aromatic rings on the same cross-linker molecule. In embodiments where the boronic acid moieties are attached to different aromatic rings, the aromatic rings may be separated by a linker. The linker may include a polymer core, such as any of the polymer backbones described herein useful for forming adhesives, such as acrylate. In such embodiments, the polymer core of the linker preferably includes about 1 to about 100 monomer units, such as about 10 to about 50 monomer units, such as about 20 to 30 monomer units. The polymer backbone can be attached to the boronic acid-containing aromatic rings through an amide linkage.

It has been discovered that the moieties can be selected and combined to control a degradation of the reversible adhesive at a predetermined pH range. In some embodiments, the boronic acid ester bond can be formed at a pH of about 7 pH to about 14 pH, such as about 7.4 pH to about 10 pH, such as about 8 pH to about 9 pH, or about 11 pH to about 12 pH. The boronic acid ester bond can be reversed at a pH of below 7 pH, such as about 1 pH to about 6 pH, such as about 2 pH to about 5 pH, such as about 3 pH to about 4 pH. The reversible adhesive formation and reversal can occur at ambient conditions, such as a temperature of about 16° C. to about 35° C., such as about 18° C. to about 26° C.

The apparel product can be submerged in a solution having a reduced pH. The pH of the solution can be adjusted by adding an acidic compound such as mannitol, such as about 80 mM to about 200 mM mannitol. In some embodiments, a pH of the solution can be controlled using any process known in the industry such as addition of HCl and/or KOH.

In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015).

In some embodiments, the reversible adhesive has a modulus of about 3 mPa to about 3500 MPa, such as about 10 mPa to about 3000 MPa, such as about 50 mPa to about 1500 mPa, such as about 90 mPa to about 125 mPa, according to tensiometric analysis using 100 N force and rate of 100 mm/min. In some embodiments, prior to crosslinking a polymer to form the reversible adhesive, the polymer has a glass transition temperature ($T_g$) of about −20° C. to about 200° C., such as about −10° C. to about 100° C., such as 10° C. to about 20° C. In some embodiments, prior to crosslinking a polymer to form the reversible adhesive, the polymer has a melting temperature ($T_m$) of about 75° C. to about 200° C., such as 100° C. to about 175° C., such as about 125° C. to about 150° C.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

In some embodiments, the reversible adhesive includes a copolymer that is a reaction product of boronic acid groups and a crosslinking group(s). In some embodiments, the crosslinking group is a disaccharide or an oligosaccharide. In some embodiments, the reversible adhesive is a reaction product of a compound having a boronic acid group having the structure shown below.

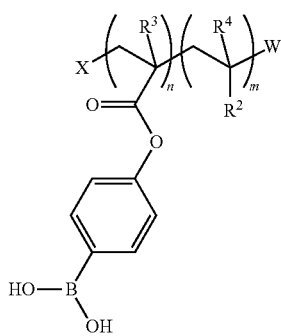

$R^1$ and $R^2$ are each independently hydrogen, a linear hydrocarbon, a cyclic hydrocarbon, or a branched hydrocarbon, such as a methyl or ethyl group. $R^3$ is a carboxyl group or a carbonyl group substituted with a linear hydrocarbon, a cyclic hydrocarbon, a branched hydrocarbon, or an ether group. In some embodiments, $R^3$ is a methacrylate or acrylate. X and W are each independently a hydrogen, a linear hydrocarbon, a cyclic hydrocarbon, or a branched hydrocarbon, such as an alkyl or aromatic group. Each of n and m are independently integers between 1 and 1000. In some embodiments, the phenyl group shown in the formula is substituted with a nitrogen containing group, an oxygen containing group, or combinations thereof. In some embodiments, $R^1$, $R^2$ and/or $R^3$ can include (meth)acrylate groups to adjust solubility, thermal properties, or combinations thereof.

In some embodiments, the reversible adhesive is a reaction product of a compound having a boronic acid group having one or more of the structures shown below.

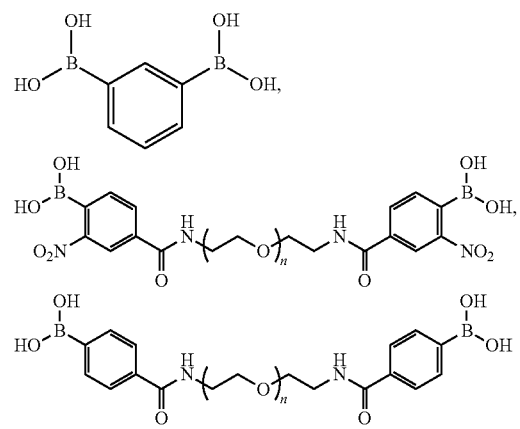

Imine Bonding

In some embodiments, the reversible adhesive includes pH reversible adhesives, such as reversible bonds produced by imine or iminium bonds. In some embodiments, the imine bonds are formed using any of the reversible adhesive backbone materials described herein, such as acrylic, methacrylic, derivatives thereof, or combinations thereof. The reversible adhesive can be formed at a pH range of about 4 pH to about 11 pH, such as a pH of about 5 to about 10, such as about 6 to about 8. The reversible adhesive can be reversed at pH below 4 or a pH above 7, such as a pH of about 1 to 2, or about 2 to about 3, or about 3 to about 4, or about 7 to about 8, or about 8 to 9, or about 9 to 10, or about 11 to 12, or about 12 to about 13, or about 13 to about 14. Upon reversal of the reversible adhesive, the reversible adhesive can form an amine and an aldehyde or a ketone. In some embodiments, the imine bond (also referred to herein as imine linkage) is formed from a polymer backbone functionalized with an aldehyde moiety, such as dextran aldehyde crosslinked with an amine or an aniline compound or moiety. In some embodiments, aldehyde-amine bonds are formed between branched polyamine and p-formylphenyl acrylate.

In some embodiments, the reversible adhesive bonds can include other pH sensitive bonds, such as thiol groups or other pH sensitive groups described herein. Other pH sensitive bonds include ketals that are labile in acidic environments, disulfides, acetals, silicon-oxygen-carbon linkages, silicon-nitrogen linkages, such as silazanes, silicon-carbon linkages, such as arylsilane, vinylsilanes, and allylsilanes, maleamates-amide bonds, ortho esters, hydrazones, activated carboxylic acid derivatives, acylhydrazones, oximes, benzoxaboroles, and combinations thereof.

In some embodiments, the reversible adhesive is prepared by reacting an amine functionalized polybutadiene with an aldehyde crosslinker to form a recyclable polybutadiene elastomer crosslinked by imine bonds. The amine groups can be grafted onto the polybutadiene via a thiol-ene reaction to form polybutadiene-$NH_2$ which can be crosslinked with benzene-1,3,5-tricarbaldehyde. The reversible adhesive can have a young's modulus of about 1 MPa to about 32 MPa, such as about 2 MPa to about 10 MPa.

In some embodiments, an imine bond is formed by a condensation reaction of a ketone group, an aldehyde group, an acyl group, and an amino group contained in a compound. In some embodiments, the imine bond is introduced into a polymer by polymerization or crosslinking reaction between reactive compounds that contain an imine bond. Reactive compounds that include imine bonds include a polyol having an imine group, a polythiol having an imine group, a polyethyleneimine, a polyamine, an isocyanate, an epoxy compound having an imine group, an alkene having an imine group, an alkyne having an imine group, or combinations thereof.

The reversible adhesive can be reversed by altering the pH outside of the formation range. Without being bound by theory, it is believed that a change in pH alters a solubility of the polymer having the imine or iminium bonds. In some embodiments, the apparel products having the reversible bonds can be submerged in a solution having a pH outside of the pH range at which the reversible adhesive is formed. The pH of the solution can be tuned, altered, or buffered by adding one or more of carboxylic acids, imidazole, pyridine, phenols, polyamines, or combinations thereof. In some embodiments, the solution includes an acid-base catalyst including one or more of an inorganic acid, organic acid, and acid salt catalyst thereof. Inorganic acids include sulfuric acid, hydrochloric acid, phosphoric acid, or combinations thereof. Organic acids include methanesulfonic acid, benzenesulfonic acid, p-toluenesulfonic acid, and combinations thereof. Salt catalysts include sulfate, hydrogen sulfate, and hydrogen phosphate. The reversible adhesive formation and reversal can occur at ambient conditions, such as a temperature of about 16° C. to about 35° C., such as about 18° C. to about 26° C. In some embodiments, the apparel product is submerged for about 1 second to about 1 hour, such as about 10 seconds to about 10 minutes, such as about 30 seconds to about 50 minutes.

In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015).

In some embodiments, the reversible adhesive has a modulus of about 3 mPa to about 3500 MPa, such as about 10 mPa to about 3000 MPa, such as about 50 mPa to about 1500 mPa, such as about 90 mPa to about 125 mPa, according to tensiometric analysis using 100 N force and rate of 100 mm/min. In some embodiments, prior to crosslinking a polymer to form the reversible adhesive, the polymer has a glass transition temperature ($T_g$) of about −20° C. to about 200° C., such as about −10° C. to about 100° C., such as 10° C. to about 20° C. In some embodiments, prior to crosslinking a polymer to form the reversible adhesive, the polymer has a melting temperature ($T_m$) of about 75° C. to about 200° C., such as 100° C. to about 175° C., such as about 125° C. to about 150° C.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

In a particular example synthesis of the reversible adhesive, a solution can be prepared by combining p-hydroxybenzaldehyde (e.g., 5 g, 41 mmol), triethylamine (6.5 mL), and dichloromethane (DCM) (50 mL). Acryloyl chloride (4.5 g, 50 mmol) can be dissolved in 10 mL of DCM and added dropwise to the solution. The reaction carried out in room temperature for about 12 hours. The trimethylamine hydrochloride was removed by filtration, extracted with saturated $NaHCO_3$, and the organic phase was dried with $Na_2SO_4$ and the p-formylphenyl acrylate was collected by rotary evaporation.

The extracted p-formylphenyl acrylate was combined with 100 mL of methanol and 10 g, 112 mmol branched polyamine $PA_{6N}$ to form a second solution. Branched polyamines can be formed from reacting methyl acrylate with an amine selected from ethylenediamine, diethylenetriamine, tris(2-aminoethyl)amine, triethylenetetramine, tetraethylenepentamine, or combinations thereof. $PA_{6N}$ can be formed from triethylenetetramine. The second solution can be heated and a reaction can occur over about 12 hours. A composition is collected by rotary evaporation. The molar ratio of polyamine to p-formylphenyl acrylate can be about 1:5 to about 1:2, such as about 1:4 to about 2:5.

The composition is cured at a temperature of about 0° C. to about 100° C., such as about 16° C. to about 30° C. to form the reversible adhesive. The composition can be deposited on a portion of the major component or a portion of the minor component. The major component and the minor component can be coupled together via the composition. The composition can be cured with or without the presence of pressure. In some embodiments a pressure of about 1 kPa to about 10 kPa, such as about 3 kPa to about 7 kPa can be applied between the components. The composition can be cured in about 12 hours to about 36 hours, such as about 18 hours to about 24 hours.

Shape Memory Materials

In some embodiments, the reversible adhesives are reversible upon exposure to light, such as ultraviolet light or heat. In some embodiments, the reversible adhesive is at least partially composed of a shape memory material, such as azobenzene, spiropyran, or combinations thereof incorporated into one or more polymers described relative to the polymer backbone materials described herein. In some embodiments, the reversible adhesive includes one or more of the polymer backbone materials described herein, such as acrylic or methacrylic acid monomers, derivatives thereof (e.g., esters and amides) thereof. In some embodiments, the reversible adhesive further includes light emitting material, such as electroluminescence particles. In some embodiments, the reversible adhesive includes a conductive material. The conductive material is configured to convey electricity to the light emitting material which illuminates upon application of the electricity. The light emitted from the light emitting material can deactivate the bonds of the shape memory material to reverse the adhesion of the reversible adhesive.

In some embodiments, the conductive material is a carbon nanomaterial, a silver nanomaterial, a conductive metal, or combinations thereof. In some embodiments, the conductive material is present in the reversible adhesive in an amount of about 1 wt. % to about 90 wt. %, such as about 10 wt. % to about 80 wt. %, such as about 20 wt. % to about 70 wt. %, such as about 30 wt. %. In some embodiments, the light emitting material is present in the reversible adhesive in an amount of about 1 wt. % to about 90 wt. %, such as about 10 wt. % to about 80 wt. %, such as about 20 wt. % to about 70 wt. %, such as about 30 wt. %. The shape memory material is configured to liquefy when exposed to a light having a wavelength of about 100 nm to about 600 nm, such as about 300 nm to about 400 nm.

Alternatively, the reversible adhesive can include any of the backbone polymers described herein and the backbone polymer can be impregnated or doped with shape memory materials, such as a plurality of linearly shaped or oriented shape memory materials to conform to the surface of the component on which the reversible adhesive is applied. During disassembly of the apparel products, a heat is applied to the reversible adhesive which restores the shape memory to its original shape that is three dimensional and is random relative to the surface of the component on which the reversible adhesive is applied. The heat can be localized to the reversible adhesive using the methods described herein relative to particles (e.g., 204 shown in FIG. 2). In some embodiments, the reversible adhesive includes the shape memory materials in an amount of about 1 wt. % to about 90 wt. %, such as about 10 wt. % to about 80 wt. %, such as about 20 wt. % to about 70 wt. %, such as about 30 wt. %.

In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015).

In some embodiments, the reversible adhesive has a modulus of about 3 mPa to about 3500 MPa, such as about 10 mPa to about 3000 MPa, such as about 50 mPa to about 1500 mPa, such as about 90 mPa to about 125 mPa, according to tensiometric analysis using 100 N force and rate of 100 mm/min. In some embodiments, prior to crosslinking a polymer to form the reversible adhesive, the polymer has a glass transition temperature ($T_g$) of about −20° C. to about 200° C., such as about −10° C. to about 100° C., such as 10° C. to about 20° C. In some embodiments, prior to crosslinking a polymer to form the reversible adhesive, the polymer has a melting temperature ($T_m$) of about 75° C. to about 200° C., such as 100° C. to about 175° C., such as about 125° C. to about 150° C.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

In some embodiments, the reversible adhesive includes a metal including gold/cadmium alloy, titanium/nickel alloy, copper/aluminum alloy, and the like, and a shape memory polymer including polyurethane, polyethylene, epoxy, polystyrene, or combinations thereof.

In some embodiments, the shape memory material can be a plurality of particles, the particles having an average longest dimension of about 20 μm to about 500 μm, such as about 50 μm to about 400 μm, such as about 100 μm to about 300 μm.

An example shape memory material can be formed by mixing Poly(Bisphenol A-co-epichlorohydrin), glycidyl end capped with a molecular weight of 1075 g/mol, and a liquid bisphenol A based epoxy resin. The mixture is preheated at a temperature of about 120° C. After heating, D-230 poly (propylene glycol)bis(2-aminopropyl) ether with an average molecular weight of 230 g/mol is mixed into the preheated mixture to form a shape memory precursor. The shape memory precursor can be molded and cured at 120° C. to a predetermined shape based on the shape of the mold. The cured shape memory can be removed from the mold. The cured shape memory can be coupled to the major component or the minor component via an adhesive material.

Epoxy based shape memory materials can include an elastic modulus of about 2.5 GPa to about 10 GPa.

In some embodiments, the reversible adhesive is reversed by heating at a temperature of about 80° C. or greater, such as about 90° C. to about 200° C., such as about 100° C. to about 120° C., such as about 140° C. to about 160° C. The reversible adhesive can be exposed to heat or electromagnetic energy for about 1 second to about 24 hours, such as about 5 seconds to about 5 hours, such as about 1 minute to about 90 minutes, such as about 30 minutes to about 60 minutes.

Cyclodextrin Bonding

In some embodiments, the reversible adhesive are reversible upon exposure to light, such as ultraviolet light. The backbone can include any of the polymer backbone materials described herein, such as acrylic or methacrylic acid monomers, derivatives thereof (e.g., esters and amides) thereof. In some embodiments, the reversible adhesive includes acrylamide, acrylic acid, methyl acrylate, and 2-hydroxyethyl methacrylate. In some embodiments, the reversible adhesive is disposed on a portion of the apparel product and the portion can include stretchable fabric. The stretchable fabric can be stretched to increase area of exposure to enable penetration of light to reverse bonds.

The reversible adhesive can be formed from a first monomer having a cyclodextrin moiety, such as α-cyclodextrin, β-cyclodextrin, γ-cyclodextrin, and combinations thereof. The cyclodextrin can be bonded with a monomer having an azobenzene moiety. In some embodiments, the cyclodextrin is non-covalently and reversibly bonded to the azobenzene.

The reversible adhesive can be formed from a second monomer including the azobenzene moiety. The second comonomer can include a vinyl monomer substituent and additional groups such as alkyl groups that may have a substituent or substituents, cycloalkyl groups, and aryl groups that may have a substituent or substituents. Examples of the alkyl group of the optionally substituted alkyl group include linear, branched, or cyclic alkyl groups of $C_1$ to $C_{18}$, such as methyl, ethyl, n-propyl, isopropyl, n-butyl, isobutyl, sec-butyl, tert butyl, pentyl, cyclopentyl, hexyl, cyclohexyl, isohexyl, dodecyl, octadecyl, and adamantyl. The alkyl group may have 1 to 3 substituents, for example, such as halogen atoms (for example, such as fluorine, chlorine, and bromine), carboxyl groups, ester groups, amide groups, and hydroxyl groups that may be protected. In some embodiments, the monomer including the azobenzene moiety is di(1-azobenzenemethyleketone))-1,2-bis(4-pyridyl)ethylene.

In some embodiment, the molar ratio of the monomer including cyclodextrin to the monomer including azobenzene is about 60:1 to about 1:60, such as about 30:1 to about 20:1, or about 10:1 to about 1:1, such as about 8:1 to about 3:1, or about 1:10 to about 1:8, such as about 1:6 to about 1:3. In some embodiments, the reversible adhesive can be formed using a third monomer having adhesive properties, such as butyl acrylate or ethyl hexyl acrylate. The reversible adhesive can be formed from three monomers, the first monomer including cyclodextrin to the second comonomer including azobenzene can have a ratio of about 2:1 to about 1:2, such as about 1:1.

In some embodiments, the reversible adhesive includes a reaction product of photopolymerization initiators, such as benzophenone, 2,2-dimethoxy-1,2-diphenylethan-1-one, or combinations thereof. In some embodiments, the reversible adhesive can be applied on a component of the apparel product using any of the methods provided herein, such as patterning the adhesive using photolithography or by nozzle deposition. In some embodiments, the reversible adhesive is applied to one of the portions of a first component (e.g., minor component) to be attached to one of the portions of a second component (e.g., major component). Alternately, the reversible adhesive can be applied to both the first and second components.

The reversible adhesive can be cured by exposure to a first light having a first wavelength, such as ultraviolet light or visible light. In some embodiment, a compressive pressure is applied to the first and second component for a predetermined time after the UV light exposure until the reversible adhesive is cured, such as about 1 second to about 1 hour, such as about 10 seconds to about 10 minutes, such as about 30 seconds to about 50 minutes.

In some embodiments, the reversible adhesive can be reversed by exposure to a second light having a second wavelength different from the first wavelength used to cure the reversible adhesive, such as ultraviolet light or visible light. In some embodiments, the first light is visible light and the second light is ultraviolet light. In some embodiments, the intensity of the light exposure is greater than an intensity provided in outdoor conditions under sunlight. In some embodiments, the light intensity used to reverse the reversible adhesive is about 100 $mW/cm^2$ to about 10,000 $mW/cm^2$, such as about 800 $mW/cm^2$ to about 8,000 $mW/cm^2$, such as about 2,000 $mW/cm^2$ to about 6,000 $mW/cm^2$, such as about 4,000 $mW/cm^2$ to about 5,000 $mW/cm^2$. In some embodiments, the light used to reverse the reversible adhesive is a polarized light. The reversible adhesive can be reversed after exposure to the second light for about 1 minute to about 24 hours, such as about 10 minutes to about 20 hours, such as about 1 hour to about 6 hours.

In some embodiments, the reversible adhesive can include antioxidants or UV protectants configured to protect the reversible adhesive from reversing in ambient conditions, such as normal sun exposure.

In some embodiments, the reversible adhesive can have a T-peel strength of about 5 N/cm-width to about 100 N/cm-width, such as about 10 N/cm-width to about 50 N/cm-width, such as about 20 N/cm-width to about 30 N/cm-width, as tested according to ASTM D1876 (2015).

In some embodiments, the reversible adhesive includes multiple layers such as a primer layer disposed between the component of the apparel product and an adhesive layer that includes the reversible bonds.

In some embodiments, the reversible adhesive includes a gel having 6-acrylamide-β-cyclodextrin-derived units and N-(1-adamantyl)acrylamide-derived units at a ratio of the 6-acrylamide-β-cyclodextrin-derived units to the N-(1-adamantyl)acrylam ide-derived units of 0.3:0.4.

In some embodiments, the reversible adhesive includes a gel prepared from hyaluronic acid polymers functionalized with a photoresponsive bond between a cyclodextrin and azobenzene. Upon exposure to light, the storage modulus decreases by about 20% to about 60%, such as about 30% to about 40%.

In some embodiments, the reversible adhesive has a modulus of about 3 mPa to about 3500 MPa, such as about 10 mPa to about 3000 MPa, such as about 50 mPa to about 1500 mPa, such as about 90 mPa to about 125 mPa, according to tensiometric analysis using 100 N force and rate of 100 mm/min. In some embodiments, prior to crosslinking a polymer to form the reversible adhesive, the polymer has a glass transition temperature ($T_g$) of about −20° C. to about 200° C., such as about −10° C. to about 100° C., such as 10° C. to about 20° C. In some embodiments, prior to crosslinking a polymer to form the reversible adhesive, the polymer has a melting temperature ($T_m$) of about 75° C. to about 200° C., such as 100° C. to about 175° C., such as about 125° C. to about 150° C.

In some embodiments, prior to crosslinking a polymer to form the reversible adhesive, the polymer can have a molecular weight (e.g., weight average molecular weight) of about 700 g/mol to about 1,000,000 g/mol, such as about 1,000 g/mol to about 500,000 g/mol, such as about 10,000 g/mol to about 250,000 g/mol. The reversible adhesive after crosslinking can have polymer(s) having a much higher molecular weight than before crosslinking because, after crosslinking, multiple polymer molecules are crosslinked together.

In some embodiments, the reversible adhesive includes a first viscosity and a first solubility in a solvent. The reversible adhesive after treating the reversible adhesive with a deactivating condition has a second viscosity. The second viscosity can be less than the first viscosity, such as about 10% to about 99% less, such as about 20% to about 90% less, such as about 40% to about 80% less, such as about 60% to about 75% less. The reversible adhesive after treating the reversible adhesive can have a second solubility higher than the first solubility in a solvent. In some embodiments, the reversible adhesive before treating is not soluble in a solvent, such as an organic solvent, and the reversible adhesive after treating is soluble in the solvent (at the same temperature and pressure conditions as that of the reversible adhesive before treating).

The reversible adhesive used to join components can include a mixture of one or more of the reversible adhesives described herein, such as a temperature reversible adhesive (such as a Diels-Alder reversible adhesive), a chemical reversible adhesive (such as disulfide reversible adhesive), a thioester reversible adhesive, a boronic acid reversible adhesive, imine reversible adhesive, light reversible adhesive (such as cyclodextrin-azobenzene reversible adhesive), shape memory reversible adhesive.

Overall, a number of different chemistries can be incorporated into the reversible adhesive to provide controlled disassembling of the products in a streamlined large-scale process. The apparel products described herein can include a number of different components that can be joined together by the reversible adhesive and separated from one another using the methods described herein depending on the composition of the apparel product components.

Additional Aspects

The present disclosure can include the following non-limiting aspects and/or embodiments:

Clause A1. A method of disassembling an apparel product, comprising: exposing an adhesive of the apparel product to heat or electromagnetic energy, the adhesive being dis- posed at least partially disposed between a major component and a minor component of the apparel product, the adhesive comprising a shape memory material, the major component forming a base portion of the apparel product and configured to be supported and worn at least partially over a portion of a wearer, and the minor component forming a secondary portion configured to be coupled to the major component with the adhesive; and separating the major component from the minor component adjoined by the adhesive.

Clause A2. The method of Clause A1, wherein the shape memory material is selected from the group consisting of an azobenzene, a spiropyran, and combinations thereof.

Clause A3. The method of Clause A1 or Clause A2, wherein the shape memory material is incorporated into a polymer having acrylic monomeric units, derivatives thereof, esters thereof, amides thereof, or combinations thereof.

Clause A4. The method of any of Clauses A1 to A3, wherein the adhesive further comprises a light emitting material and a conductive material, wherein exposing the apparel product to electromagnetic energy comprises providing electricity to the conductive material and illuminating the light emitting material.

Clause A5. The method of any of Clauses A1 to A4, wherein exposing the adhesive to heat comprises heating the shape memory material, wherein the shape memory material changes shape upon exposure to heat.

Clause A6. The method of any of Clauses A1 to A5, wherein the apparel product is selected from the group consisting of a shirt, a pant, a skirt, a coat, a dress, a sweater, a body suit, and combinations thereof.

Clause A7. The method of any of Clauses A1 to A6, wherein the major component comprises a material selected from the group consisting of a polyester, a polyamide, a cotton, mixtures thereof, and combinations thereof.

Clause A8. The method of any of Clauses A1 to A7, wherein the adhesive has a T-peel strength of about 5 N/cm-width to about 100 N/cm-width.

Clause A9. The method of any of Clauses A1 to A8, wherein the shape memory material comprises a polymer selected from the group consisting of a polyurethane, an epoxy, a polyethylene, and combinations thereof.

Clause A10. The method of any of Clauses A1 to A9, wherein the shape memory material transitions from a solid to liquid state upon exposure to the electromagnetic energy.

Clause A11. The method of any of Clauses A1 to A10, wherein the electromagnetic energy is a light having a wavelength of about 100 nm to about 600 nm.

Clause A12. The method of any of Clauses A1 to A11, further comprising sorting the separated major component and the minor component by density.

Clause A13. The method of any of Clauses A1 to A12, further comprising sorting the separated major component and the minor component by color.

Clause A14. The method of any of Clauses A1 to A13, wherein the adhesive is impregnated or doped with the shape memory material.

Clause A15. The method of any of Clauses A1 to A14, wherein the shape memory material comprises a plurality of linearly shaped or oriented particles.

Clause A16. A method of disassembling an apparel product, comprising: exposing an adhesive comprising a shape memory material to an electromagnetic energy, the adhesive being disposed at least partially between a major component and a minor component of the apparel product, wherein the composition weakens bonding between the main component and the minor component, the major component forming a base portion of the apparel product and configured to be supported and worn at least partially over a portion of a wearer, and the minor component forming a secondary portion configured to be coupled to the major component with the adhesive; and separating the major component from the minor component adjoined by the adhesive, the major component comprising synthetic or natural fibers, wherein the major component or minor component comprises recyclable material.

Clause A17. The method of Clause A16, further comprising separating the adhesive from the major component and the minor component, wherein separating the adhesive comprises applying a centrifugal force to the apparel product for about 1 minute to about 30 minutes.

Clause A18. The method of Clause A16 or Clause A17, wherein exposing the adhesive to the electromagnetic energy comprises stretching the major component or the minor component on either side of the adhesive and exposing the stretched major component or minor component to a light.

Clause A19. The method of any of Clauses A16 to A18, wherein the adhesive includes the shape memory material in an amount of about 20 wt. % to about 70 wt. %.

Clause A20. A method of disassembling apparel products, the method comprising: heating a plurality of apparel products, each apparel product of the plurality of apparel products having an adhesive comprising a shape memory disposed between a major component and a minor component of each apparel product of the plurality of apparel products, each of the major components forming a base portion of the apparel product and configured to be supported and worn at least partially over a portion of a wearer, and each of the minor components forming a secondary portion configured to be coupled to a respective major component with the adhesive; and applying a centrifugal force to the plurality of apparel products.

Clause B1. A method of assembling an apparel product, comprising: applying a composition to a portion of a major component of the apparel product or a portion of a minor component of the apparel product; coupling the portion of the minor component with the portion of the major component via the composition, the major component forming a base portion of the apparel product and configured to be supported and worn at least partially over a portion of a wearer, and the minor component forming a secondary portion configured to be coupled to the major component with an adhesive; and converting the composition to form the adhesive and the apparel product, the adhesive comprising a shape memory material.

Clause B2. The method of Clause B1, further comprising doping the adhesive or the composition with particles capable of absorbing electromagnetic energy and converting the electromagnetic energy to thermal energy.

Clause B3. The method of Clause B1 or B2, wherein the particles comprise an iron-containing material.

Clause B4. The method of any of Clauses B1 to B3, wherein the shape memory material is configured to transition from a first state to a second state when exposed to the thermal energy.

Clause B5. The method of Clause B4, wherein the first state is a first shape and the second state is a second shape.

Clause B6. The method of Clause B4, wherein the first state is a first solid state and the second state is a liquid state or a second solid state having a higher solubility than the first solid state.

Clause B7. The method of any of Clauses B1 to B6, wherein the composition is applied such that the adhesive has a thickness of about 0.025 mm to about 5 mm.

Clause B8. The method of any of Clauses B1 to B7, wherein curing the composition comprises reducing a temperature of the composition.

Clause B9. The method of any of Clauses B1 to B8, wherein curing the composition comprises applying a force by pressing the portion of the major component against the portion of the minor component.

Clause B10. A method of assembling an apparel product, comprising: applying a composition to a portion of a major component of the apparel product or a portion of a minor component of the apparel product; doping the composition with particles after applying the composition to the portion of the major component or the portion of the minor product; coupling the portion of the minor component with the portion of the major component via the composition, the major component forming a base portion of the apparel product and configured to be supported and worn at least partially over a portion of a wearer, and the minor component forming a secondary portion configured to be coupled to the major component with an adhesive; and converting the composition to form the adhesive and the apparel product, the adhesive comprising a shape memory material.

Clause B11. The method of Clause B10, wherein applying the composition comprises applying the composition by a heat gun, printing, spraying, painting, dipping, roll on, screen printing, or combinations thereof.

Clause B12. The method of Clause B10 or B11, wherein the particles are selected from the group consisting of magnetic particles, electroluminescence particles, and combinations thereof.

Clause B13. The method of any or Clauses B10 to B12, wherein the shape memory material comprises a material selected from the group consisting of an azobenzene, a spiropyran, and a combination thereof.

Clause B14. The method of any of Clauses B10 to B13, wherein doping comprises forming a concentration of magnetic particles that is highest at a center third of a thickness of the composition, the thickness of the composition is measured from the major component to the minor component.

Clause B15. A method of assembling an apparel product, comprising: forming a composition; applying the composition to a portion of a major component of the apparel product or a portion of the minor component of the apparel product; coupling the portion of the minor component with the portion of the major component via the composition, the major component forming a base portion of the apparel product and configured to be supported and worn at least partially over a portion of a wearer, and the minor component forming a secondary portion configured to be coupled to the major component with an adhesive comprising the shape memory material; and converting the composition to form the adhesive and the apparel product.

Clause B16. The method of Clause B15, wherein the shape memory material comprises a plurality of particles comprising an average longest dimension of about 20 µm to about 500 µm.

Clause B17. The method of Clause B15 or Clause B16, wherein forming the composition comprising shape memory material comprises incorporating the shape memory material into a polymer selected from the group consisting of a polyurethane, a polyethylene, an epoxy, a polypropylene, and combinations thereof.

Clause B18. The method of any of Clauses B15 to B17, wherein the adhesive further comprises magnetic particles selected from the group consisting of $Fe_3O_4$, $\gamma\text{-}Fe_2O_3$, metallic iron, cobalt, nickel, FeN, FePt, FePd, and combinations thereof.

Clause B19. The method of any of Clauses B15 to B18, further comprising loading the shape memory material into the composition in an amount of about 1 wt. % to about 70 wt. % on a weight basis of total weight of the composition.

Clause B20. The method of any of Clauses B15 to B19, wherein the adhesive further comprises a conductive material.

Clause C1. An apparel product, comprising: a major component forming a base portion of the apparel product and configured to be supported and worn at least partially over a portion of a wearer; a minor component forming a secondary portion configured to be coupled to the major component; and an adhesive disposed at least partially between a portion of the major component and a portion of the minor component, the adhesive comprising a shape memory material.

Clause C2. The apparel product of Clause C1, wherein the apparel product is selected from the group consisting of a shirt, a pant, a skirt, a coat, a dress, a sweater, a body suit, and combinations thereof.

Clause C3. The apparel product of Clause C1 or Clause C2, wherein the major component comprises a material selected from the group consisting of a polyester, a polyamide, a cotton, mixtures thereof, and combinations thereof.

Clause C4. The apparel product of any of Clauses C1 to C3, wherein the adhesive has a thickness of about 0.025 mm to about 5 mm.

Clause C5. The apparel product of any of Clauses C1 to C4, wherein the adhesive comprises particles selected from the group consisting of magnetic particles, electroluminescence particles, and combinations thereof.

Clause C6. The apparel product of any of Clauses C1 to C5, wherein the shape memory material comprises a material selected from the group consisting of an azobenzene, a spiropyran, and combinations thereof.

Clause C7. The apparel product of any of Clauses C1 to C6, wherein the adhesive comprises a concentration of shape memory material that is highest at a center third of a thickness of the composition, the thickness of the composition is measured from the major component to the minor component.

Clause C8. The apparel product of any of Clauses C1 to C7, wherein the adhesive has a T-peel strength of about 5 N/cm to about 100 N/cm.

Clause C9. The apparel product of any of Clauses C1 to C8, wherein the major component or the minor component is composed of a recyclable material.

Clause C10. An apparel product, comprising: a major component of the apparel product, the major component forming a base portion of the apparel product and configured to be supported and worn at least partially over a portion of a wearer; a minor component of the apparel product forming a secondary portion configured to be coupled to the major component; and an adhesive disposed on a portion of the major component or the minor component of the apparel product, the adhesive comprising a polymer; a shape memory material; and a plurality of particles.

Clause C11. The apparel product of Clause C10, wherein the polymer comprises monomeric units selected from the group consisting of an acrylate, a methacrylate, an acrylic, an ethylene, a propylene, a styrene, a vinyl acetate, a vinyl ester monomers, and combinations thereof.

Clause C12. The apparel product of Clause C10 or Clause C11, wherein the plurality of particles are selected from the group consisting of magnetic particles, electroluminescence particles, and combinations thereof.

Clause C13. The apparel product of any of Clauses C10 to C12, wherein the adhesive further comprises a conductive material selected from the group consisting of gold, cadmium, titanium, nickel, copper, aluminum, alloys thereof, and combinations thereof.

Clause C14. The apparel product of any of Clauses C10 to C13, wherein the shape memory material is selected from the group consisting of a polyurethane shape memory material, a polyethylene shape memory material, an epoxy shape memory material, a polystyrene shape memory material, and combinations thereof.

Clause C15. An apparel product, comprising: a major component forming a base portion of the apparel product and configured to be supported and worn at least partially over a portion of a wearer; a minor component forming a secondary portion configured to be coupled to the major component; and an adhesive disposed on a portion of the major component or the minor component of the apparel product, the adhesive comprising a polymer doped with shape memory material having a first state.

Clause C16. The apparel product of Clause C15, wherein the adhesive further comprises one or more additives in an amount of about 1 wt. % to about 40 wt. % of total additives on a basis of total weight of the adhesive based on the polymer, the shape memory material, and the one or more additives.

Clause C17. The apparel product of Clause C15 or Clause C16, wherein at least one of the one or more additives is a tackifier.

Clause $C_{18}$. The apparel product of any of Clauses C15 to C17, wherein the adhesive further comprises a polyurethane matrix, wherein the polymer is incorporated into the polyurethane matrix.

Clause C19. The apparel product of any of Clauses C15 to C18, wherein the shape memory material is configured to transition to a second state upon exposure to electromagnetic energy or heat energy.

Clause C20. The apparel product of any of Clauses C15 to C19, wherein the adhesive comprises the shape memory material in an amount of about 1 wt. % to about 70 wt. % on a weight basis of total weight of the adhesive.

In the current disclosure, reference is made to various embodiments. However, it should be understood that the present disclosure is not limited to specific described embodiments. Instead, any combination of the following features and elements, whether related to different embodiments or not, is contemplated to implement and practice the teachings provided herein. Additionally, when elements of the embodiments are described in the form of "at least one of A and B," it will be understood that embodiments including element A exclusively, including element B exclusively, and including element A and B are each contemplated. Furthermore, although some embodiments may achieve advantages over other possible solutions or over the prior art, whether or not a particular advantage is achieved by a given embodiment is not limiting of the present disclosure. Thus, the aspects, features, embodiments and advantages disclosed herein are merely illustrative and are not considered elements or limitations of the appended claims except where explicitly recited in a claim(s).

While the foregoing is directed to embodiments of the present disclosure, other and further embodiments of the disclosure may be devised without departing from the basic scope thereof, and the scope thereof is determined by the claims that follow.

What is claimed is:
1. An apparel product, comprising:
 a first component forming a base portion of the apparel product;
 a second component; and
 an adhesive coupling a portion of the first component and a portion of the second component, the adhesive comprising a shape memory material incorporated in or coupled to one or more polymer backbones, wherein the adhesive is configured to deactivate responsive to electromagnetic energy, microwave radiation, or ultraviolet radiation.

2. The apparel product of claim 1, wherein the apparel product is a shirt.

3. The apparel product of claim 1, wherein the first component comprises a material selected from the group consisting of a polyester, a polyamide, a cotton, mixtures thereof, and combinations thereof.

4. The apparel product of claim 1, wherein the adhesive has a thickness of about 0.025 mm to about 5 mm.

5. The apparel product of claim 1, wherein the adhesive further comprises electroluminescence particles.

6. The apparel product of claim 1, wherein the shape memory material comprises a spiropyran.

7. The apparel product of claim 1, wherein the adhesive comprises a concentration of shape memory material that is highest at a center third of a thickness of the adhesive, the thickness of the adhesive is measured from the first component to the second component.

8. The apparel product of claim 1, wherein the adhesive has a T-peel strength of about 5 N/cm to about 100 N/cm.

9. The apparel product of claim 1, wherein the first component or the second component is composed of a recyclable material.

10. An apparel product, comprising:
 a first component of the apparel product, the first component forming a base portion of the apparel product;
 a second component of the apparel product forming a secondary portion configured to be coupled to the first component; and an adhesive disposed on a portion of the first component or the second component of the apparel product, wherein the adhesive is configured to deactivate responsive to electromagnetic energy, microwave radiation, or ultraviolet radiation, the adhesive comprising:
a polymer;
a shape memory material; and
a plurality of particles.

11. The apparel product of claim 10, wherein the polymer comprises monomeric units selected from the group consisting of an acrylate, a methacrylate, an acrylic, an ethylene, a propylene, a styrene, a vinyl acetate, a vinyl ester monomers, and combinations thereof.

12. The apparel product of claim 10, wherein the plurality of particles are selected from the group consisting of magnetic particles, electroluminescence particles, and combinations thereof.

13. The apparel product of claim 12, wherein the adhesive further comprises a conductive material selected from the group consisting of gold, cadmium, titanium, nickel, copper, aluminum, alloys thereof, and combinations thereof.

14. The apparel product of claim 10, wherein the shape memory material is selected from the group consisting of a polyurethane shape memory material, a polyethylene shape memory material, an epoxy shape memory material, a polystyrene shape memory material, and combinations thereof.

15. An apparel product, comprising:
a first component forming a base portion of the apparel product;
a second component forming a secondary portion configured to be coupled to the first component; and
an adhesive disposed on a portion of the first component or the second component of the apparel product, the adhesive comprising a polymer doped with shape memory material having a first state, wherein the adhesive is configured to deactivate responsive to electromagnetic energy, microwave radiation, or ultraviolet radiation.

16. The apparel product of claim 15, wherein the adhesive further comprises one or more additives in an amount of about 1 wt. % to about 40 wt. % of total additives on a basis of total weight of the adhesive based on the polymer, the shape memory material, and the one or more additives.

17. The apparel product of claim 16, wherein at least one of the one or more additives is a tackifier.

18. The apparel product of claim 15, wherein the adhesive further comprises a polyurethane matrix, wherein the polymer is incorporated into the polyurethane matrix.

19. The apparel product of claim 15, wherein the shape memory material is configured to transition to a second state upon exposure to electromagnetic energy, microwave radiation, or ultraviolet radiation, and wherein transitioning to the second state causes the adhesive to deactivate.

20. The apparel product of claim 15, wherein the adhesive comprises the shape memory material in an amount of about 1 wt. % to about 70 wt. % on a weight basis of total weight of the adhesive.

* * * * *